(12) United States Patent
Andrali et al.

(10) Patent No.: US 9,597,337 B2
(45) Date of Patent: Mar. 21, 2017

(54) BERBERINE-URSODEOXYCHOLIC ACID CONJUGATE FOR TREATING THE LIVER

(71) Applicant: NORTH AMERICAN BIOMEDICAL RESEARCH CENTER USA, INC., Los Angeles, CA (US)

(72) Inventors: Shiva Sreenath Andrali, Los Angeles, CA (US); Venkatesh Tekumalla, Hyderabad (IN)

(73) Assignee: NORTH AMERICAN BIOMEDICAL RESEARCH CENTER USA, INC., Los Angeles, CA (US)

( * ) Notice: Subject to any disclaimer, the term of this patent is extended or adjusted under 35 U.S.C. 154(b) by 0 days.

(21) Appl. No.: 15/077,661

(22) Filed: Mar. 22, 2016

(65) Prior Publication Data
US 2016/0199391 A1    Jul. 14, 2016

Related U.S. Application Data

(63) Continuation-in-part of application No. 14/864,226, filed on Sep. 24, 2015, now abandoned, which is a continuation of application No. 14/245,722, filed on Apr. 4, 2014, now abandoned.

(51) Int. Cl.
*A61K 31/4745* (2006.01)
*A61K 31/58* (2006.01)
*A61K 9/00* (2006.01)
*C07J 43/00* (2006.01)
*C07D 491/147* (2006.01)
*C07J 9/00* (2006.01)

(52) U.S. Cl.
CPC .......... *A61K 31/58* (2013.01); *A61K 9/0019* (2013.01); *A61K 9/0053* (2013.01); *C07D 491/147* (2013.01); *C07J 43/003* (2013.01); *C07J 9/005* (2013.01)

(58) Field of Classification Search
USPC ....................................................... 514/280
See application file for complete search history.

(56) References Cited

FOREIGN PATENT DOCUMENTS

CN    102225961 A    10/2011

*Primary Examiner* — Charanjit Aulakh
(74) *Attorney, Agent, or Firm* — Hankin Patent Law, APC; Anooj Patel; Kevin Schraven

(57) ABSTRACT

The present invention is a method and compound for treating specific cancerous cell lines. The invention treats liver cancer by directing a cancer-fighting drug into the liver hepatoportal circuit. The cancer-fighting drug is attached to a naturally produced molecule which functions primarily in the hepatoportal circuit and has organotropism for the hepatoportal circuit.

10 Claims, 21 Drawing Sheets

BERBERINE-URSODEOXYCHOLIC ACID CONJUGATE FOR TREATING THE LIVER

CROSS-REFERENCE TO RELATED APPLICATIONS

This Continuation-In-Part Patent Application claims the benefit of U.S. Non-Provisional Patent Application No. 14/864,226, filed on Sep. 24, 2015, titled "BERBERINE-URSODEOXYCHOLIC ACID CONJUGATE FOR TREATING THE LIVER," by inventors Shiva Sreenath Andrali and Venkatesh Tekumalla, which claims the benefit of U.S. Non-Provisional patent application Ser. No. 14/245,722, filed on Mar. 4, 2014, titled "BERBERINE-URSODEOXYCHOLIC ACID CONJUGATE FOR TREATING THE LIVER," by inventors Shiva Sreenath Andrali and Venkatesh Tekumalla, the contents of which are expressly incorporated herein by this reference as though set forth in their entirety.

FIELD OF INVENTION

This invention relates to a method and molecule for treating solid tumors. More particularly, the invention relates to the synthesis of and molecule, berberine-ursodeoxycholic acid conjugate, herein referred to as NABR01, for specifically targeting and treating cancerous liver cells. NABR01 is easily administered, increases effectiveness, and may lower negative side-effects relative to other available liver ailment and cancer fighting techniques.

BACKGROUND

For centuries, people have attempted to cure ailments and diseases with whatever means they had available at the time. Initially, this could include rituals or sacred procedures. As time progressed, people started to discover the efficacy of certain herbs, roots, and other naturally occurring substances in the treatment of ailments. As civilization progressed even further, science allowed for humans to discover what made the herbs and roots so effective. Useful and effective compounds were identified, isolated, purified, and administered with great efficacy in the treatment of diseases.

People then discovered they could actually create compounds, based both on knowledge gleaned from their past in combination with knowledge gained from scientific experimentation. With this new creative ability, diseases were fought on massive scales, and deaths as a result dropped drastically. As of now, two diseases were even fought to eradication, smallpox and rinderpest, and numerous other diseases are believed to be just a few years away from eradication. Yet, certain diseases are more difficult to treat, and some are even the result of an individual's behavior, so they cannot be eradicated purely through the use of treatment. In many cases, they must be fought as they appear in the individual.

Of particular importance is the human liver. The liver is has a myriad of functions in the body which comprises cleaning toxins from blood, regulating bodily functions, producing substances for proper digestion, producing regulatory signal molecules, and even facilitating blood clotting. The liver also has the unique ability to function even if a significant portion has been removed. However, with the myriad of functions performed by the liver, there are also a myriad of ailments which may affect the liver and its ability to function.

There are a myriad of ailments that may be experienced due problems in the liver which comprises cancer, cirrhosis, primary sclerosing, cholangitis, cholelithiasis, non-alcoholic fatty liver disease, non-alcoholic steatohepatitis, high cholesterol, cardiovascular conditions and diabetes. Various medicines and treatments have been created in order to combat these conditions, but they experience similar issues as other medicines and treatments. Through diligent research and enormous efforts, many useful molecules have been and are being discovered. This may have resulted in a double edged sword, as now there are a voluminous amount of useful molecules or suspected useful molecules, but as a consequence, there are virtually an infinite number of combinations using these molecules. Certain molecules or drugs have beneficial effects when combined with other molecules, but without going through rigorous experimentation, often including costly and expensive human trials, many of these combinations are, and will remain, undiscovered. The problem with combining molecules, however, is that the results can be hard to predict, and in many cases can cause more harm than good. Many drugs may be used subsequently without disastrous side-effects, but concurrently taking an effective dose of that same drug can result in serious side-effects, including death. As a result, experimentation must be done slowly and deliberately which may result in discovering non-useful formulations. The cost and danger associated with experimentally combining different drugs in a patient can be both extremely costly, and more importantly, extremely dangerous.

Further, although it is known that combining different molecules in a single drug treatment compound is theoretically possible, it is not possible to predict with certainty what the combination may do. Because there are a multitude of biochemical pathways in the body, most experiments are done in vitro under conditions that the experimenter believes may be relevant. Once data is acquired, and there is some level of confidence in what the compound actually does, experiments with live patients or other organisms may be started. However, due to the complexity of a fully functioning host, the compound may interfere or react with pathways wholly unaccounted for in the in vitro trials. Even though two molecules appear to act on different biochemical pathways, it is possible that, in combination, they will wholly inhibit a completely different pathway, whereas, when alone, they would only inhibit one part of the pathway which the body could compensate for by using an alternate pathway. Thereby, the pathway in danger of being shut down would be undetected until the two drugs are used in conjunction.

Even with all the medication at our disposal, patients are fighting and living with cancer and other liver ailments, often for the rest of their lives. Often, the drugs are simply not effective enough to cure the cancer or the ailment completely and finding methods of combining drugs to increase effectiveness is extremely slow, costly, difficult, and often fruitless work.

Chinese Patent Application Publication No. 102225961A discloses a molecule comprising berberine and ursodeoxycholic acid with a linker of indeterminate length. This reference broadly states that the compound is useful for treating tumors, but this reference lacks instructive information or specific details that would be critical in determining the utility of the molecule, and a person of ordinary skill in the art would not reasonably consider this reference when designing molecules to combat specific forms of liver cancer due to its lack of information and data. Additionally, the tumors referenced could relate to non-cancerous tumors. The reference does not even provide any data that the disclosed molecule is, in fact, effective at anything it claims. The reference merely discloses generic molecules that may be used as carrier molecules. It is likely that even slightly different configurations of the molecule disclosed by the reference would have vastly different effects, or even no effects at all. Additionally, it is generally understood that a molecule can have vastly different effects on different medical conditions, even where the medical conditions appear to be somewhat related. Thus, even in light of this reference, a person of ordinary skill in the art would not be able to determine the usefulness, if any, of a molecule comprising berberine and ursodeoxycholic acid or effectively use any of the disclosed information to create liver cancer treatment methods.

Thus, there exists the need for effective methods and compounds for treating cancer and other liver ailments.

SUMMARY OF THE INVENTION

To minimize the limitations in the prior art, and to minimize other limitations that will become apparent upon reading and understanding the present specification, the present invention is a compound and method of creating the compound for the treatment of liver cancer and other liver ailments.

One embodiment of the present invention may be a compound of formula (Ia) below:

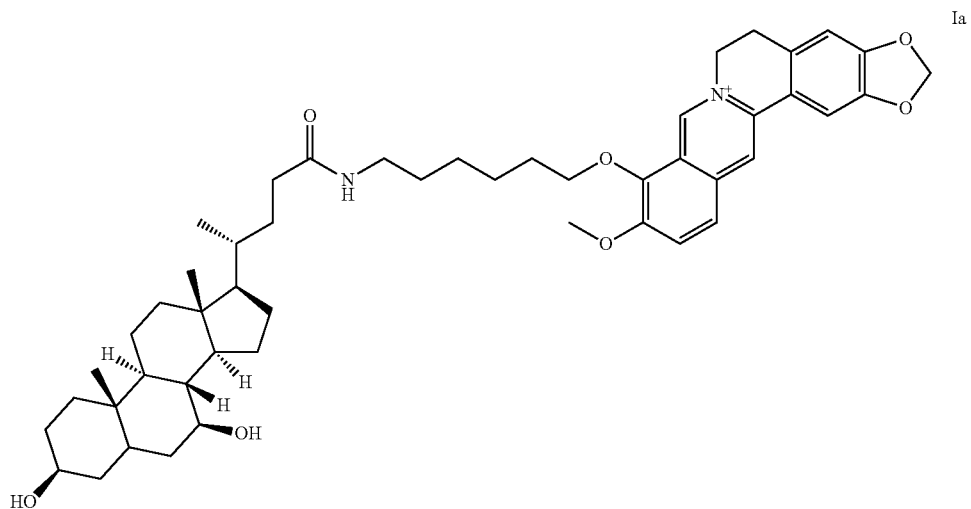 [SMILES: COc1ccc2cc3[n+](cc2c1OCCCCCCNC(=O)CC[C@@H](C)[C@H]1CC[C@H]2[C@@H]4[C@@H](O)CC5C[C@@H](O)CC[C@]5(C)[C@H]4CC[C@]12C)CCc1cc2c(cc1-3)OCO2]

One embodiment of the present invention may be A compound of formula (Ib) below:

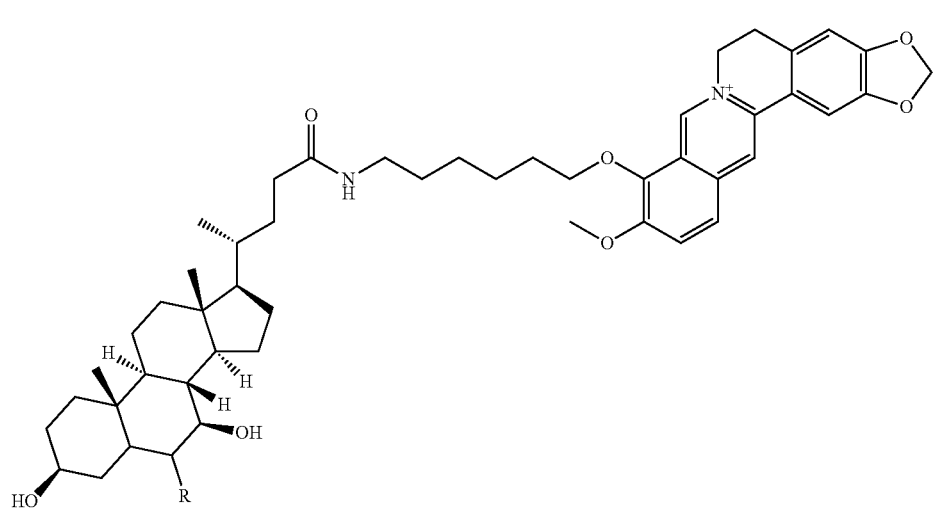

wherein an R is a functional group. The R may also be an ethyl group.

Another embodiment of the present invention may be a method of synthesizing a molecule comprising the steps: heating of compound (IIa) below

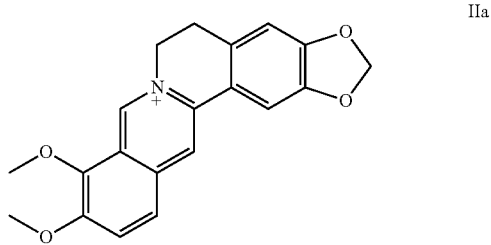 [SMILES: COc1ccc2cc3[n+](cc2c1OC)CCc1cc2c(cc1-3)OCO2]

in a reduced pressure environment to create a first synthesized compound. The method may further comprise the steps: cooling the first synthesized compound; and recrystallizing the first synthesized compound to create a crystalized solid. The method may further comprise the steps: mixing the crystallized solid with a first solvent and adding 1,6-dibromohexane to create a first mixture; heating the first mixture; diluting with a first precipitation solvent to create a first precipitate; filtering the first precipitate and washing the first precipitate with a first washing solvent to create a first crude compound. The method may further comprise the step of purifying the first crude compound to create a first purified compound. The method may further comprise the steps: dissolving the first purified compound in a second solvent; adding aqueous ammonia and ammonium chloride; and stirring to create a second mixture. The method may further comprise the step evaporating the second mixture to create a second crude compound. The method may further comprise the step purifying the second crude compound to create a second purified compound. The method may further comprise the steps: mixing the second purified compound and ursodeoxycholic acid in a third solvent to create a third mixture; and stirring the third mixture to create a fourth mixture. The method may further comprise the step diluting the fourth mixture with a third solvent and filtering to create a third crude compound. The method may further comprise the step purifying the third crude compound to create a third purified compound. The method may further comprise the step concentrating the third purified compound to create a concentrated compound.

Another embodiment of the present invention may be a method of synthesizing a molecule comprising the steps: heating of compound (IIa) below

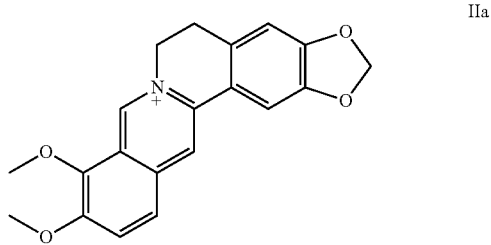 [SMILES: COc1ccc2cc3[n+](cc2c1OC)CCc1cc2c(cc1-3)OCO2]

to about 190 C. in a reduced pressure environment between 15 mmHG to 25 mmHG for a duration of about 90 minutes or more to create a first synthesized compound. The method may further comprise the steps: cooling the first synthesized compound; and recrystallizing the first synthesized compound to create a crystalized solid. The method may further comprise the steps: mixing the crystallized solid with a first solvent and adding 1,6-dibromohexane to create a first mixture; heating the first mixture to about 60 C. for about 5 hours or more; diluting with a first precipitation solvent to create a first precipitate; filtering the first precipitate and washing the first precipitate with a first washing solvent to create a first crude compound. The method may further comprise the step of purifying the first crude compound to create a first purified compound. The method may further comprise the steps: dissolving the first purified compound in a second solvent; adding aqueous ammonia and ammonium chloride; and stirring at about 70 C. for about 5 hours or more to create a second mixture. The method may further comprise the step evaporating the second mixture to create a second crude compound. The method may further comprise the step purifying the second crude compound to create a second purified compound. The method may further comprise the steps: mixing the second purified compound and ursodeoxycholic acid in a third solvent to create a third mixture; and stirring the third mixture to create a fourth mixture. The method may further comprise the step diluting the fourth mixture with a third solvent and filtering to create a third crude compound. The method may further comprise the step purifying the third crude compound to create a third purified compound. The method may further comprise the step concentrating the third purified compound to create a concentrated compound.

Another embodiment of the invention is a method of synthesizing a molecule comprising the step heating of compound (IIb) below:

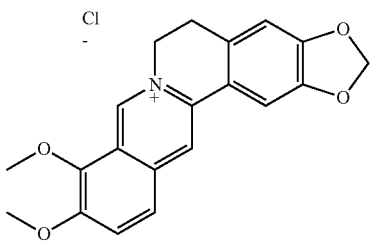

IIb to about 190 C. in a reduced pressure environment between 15 mmHG to 25 mmHG for a duration of about 90 minutes to create a first synthesized compound. The method may further comprise the steps: cooling the first synthesized compound; and adding ethanol to the first synthesized compound such that a solid present in the mixture is recrystallized to create a crystallized solid. The method may further comprise the steps mixing the crystallized solid with N,N-Dimethylformamide and adding 1,6-dibromohexane; heating to about 60 C. for about 5 hours; diluting with diethyl ether to create a first precipitate; filtering the first precipitate and washing the first precipitate with diethyl ether to create a first crude compound. The method may further comprise the step purifying the first crude compound using a neutral alumina column and a first eluent solution; wherein the first eluent solution is about 5% MeOH and 95% chloroform to create a first purified compound. The method may further comprise the steps: dissolving the first purified compound in methanol; adding approximately 25% aqueous ammonia and ammonium chloride; stirring at about 70 C. for about 5 hours to create a first mixture. The method may further comprise the step evaporating the first mixture to create a second crude compound. The method may further comprise the step purifying the second crude compound using a neutral alumina column, and a gradient elution beginning at about 5% MeOH and 95% chloroform and ending at about 12% MeOH and 88% chloroform to create a second purified compound. The method may further comprise the steps: mixing the second purified compound and ursodeoxycholic acid in N,N-Dimethylformamide; adding N,N'-Dicyclohexylcarbodiimide and DMP; and stirring at room temperature for about 24 hours to create a first reaction mix. The method may further comprise the step diluting the first reaction mix with diethyl ether and filtering to create a third crude compound. The method may further comprise the step purifying the third crude compound by using a neutral alumina column using an eluent of about 10% MeOH and 90% Chloroform to create a third purified compound. The method may further comprise the step concentrating the third purified compound by preparative thin layer chromatography to create a concentrated compound of the formula:

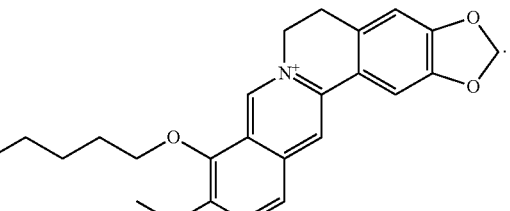

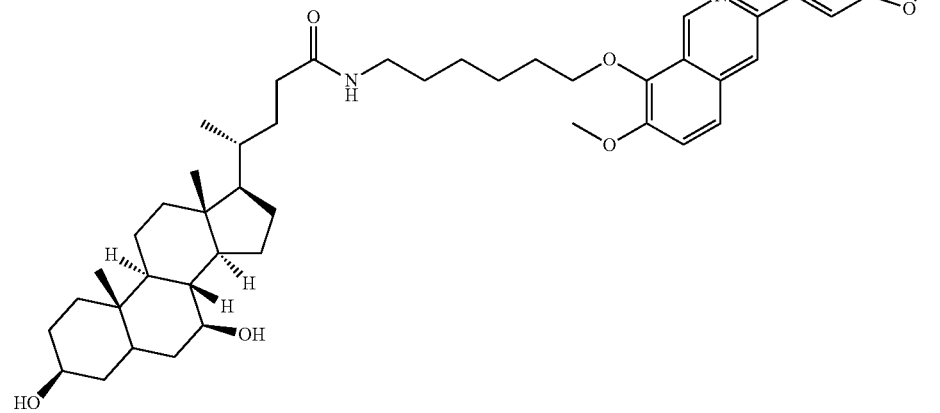

It is an object of the present invention to overcome the limitations of the prior art.

Additional embodiments of the invention will be understood from the detailed description of the invention.

DETAILED DESCRIPTION OF THE INVENTION

Figure 1:
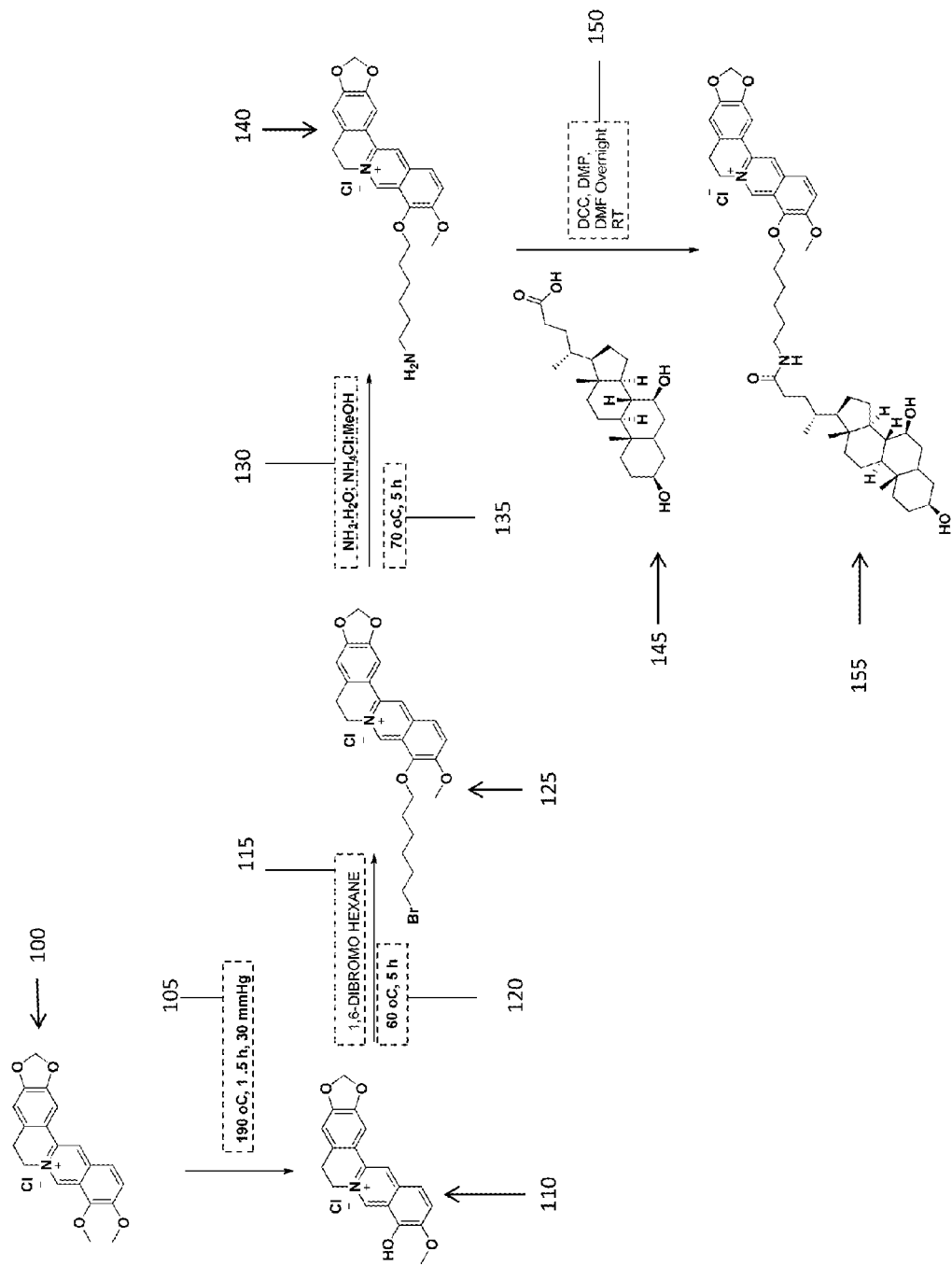
FIG. 1 is a flow diagram showing one method of synthesizing one embodiment of the invention.

In the following detailed description of various embodiments of the invention, numerous specific details are set forth in order to provide a thorough understanding of various aspects of one or more embodiments of the invention. However, one or more embodiments of the invention may be practiced without some or all of these specific details. In other instances, well-known methods, procedures, and/or components have not been described in detail so as not to unnecessarily obscure aspects of embodiments of the invention.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the figures, and the detailed descriptions thereof, are to be regarded as illustrative in nature and not restrictive. Also, the reference or non-reference to a particular embodiment of the invention shall not be interpreted to limit the scope of the invention.

The present invention is aimed at increasing the life expectancy and quality of life of people with liver cancers and other liver ailments. A compound selectively targets certain liver cancers, effectively decreasing the required dosage of therapeutic drugs and increasing effectiveness. This also means that higher, potentially dangerous dosages may not be required.

The primary components of the compound are berberine and ursodeoxycholic acid. The compound, which may be one embodiment of the invention may be called NABR01. In the following molecular structures standard methods of representing molecular structures are used. Intersections of lines and endpoints of lines represent the presence of a carbon atom. When there is a letter at the end of a line, the element represented by that letter is present, instead of a carbon. Each line represents a bond. A floating line next to a line represents a double bond. A "+" symbol represents a positive charge. A "−" symbol represents a negatives charge. C represents carbon, O represents oxygen, N represents nitrogen, H represents hydrogen, Cl represents Chlorine, Hg represents mercury, Br represents Bromine, Me represents methane or a single carbon with attached hydrogens, and R is a functional group which is variable. Dashed and bold lines represent orientation of the chemical bond, whether the bond is out of the plane or into the plane. Where a carbon is represented, but does not have a total of four bonds, hydrogens are present, as is the standard practice in drawing molecular structures. Arrows are used to indicate the order of reaction. Floating dots are used to represent electrons.

Berberine is a quaternary ammonium salt with a strong yellow coloring and is often found in plants and may have the structure:

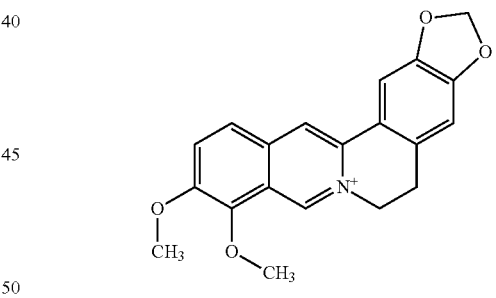

Berberine was traditionally used as a dietary supplement and has some activity as an anti-fungal agent. Additionally, berberine has been shown to have some anti-biotic effect when used in combination with other molecules such as methoxyhydnocarpin. There is some evidence that berberine is effective in treating trachoma. Berberine is also used to treat leishmaniasis. Berberine is believed to suppress proinflammatory cytokines and E-selectin. Importantly, berberine is a nucleic acid-binding isoquinolone alkaloid with wide potential therapeutic properties.

There are also many new experimental uses of berberine which implicate berberine's use in treating a wide array of ailments, comprising: diabetes mellitus; high cholesterol, nonalcoholic fatty liver disease; cardiovascular conditions; transplant rejections; cancer; depression; intestinal disorders; and human immunodeficiency virus. One proposed method of how berberine treats cancer is by berberine's ability to inhibit angiogenesis and to modulate Mcl-1, Bcl-xL, cyclooxygenase (COX)-2, MDR, tumor necrosis factor (TNF)- and IL-6, iNOS, IL-12, intercellular adhesion molecule-1 and ELAM-1 expression, MCP-1 and CINC-1, cyclin D1, activator protein (AP-1), HIF-1, PPAR-, and topoisomerase II.

The features of berberine that may be utilized by the current invention are its anti-cancer properties and anti-liver ailment properties.

Ursodeoxycholic acid is a secondary bile acid synthesized by the liver and has the structure:

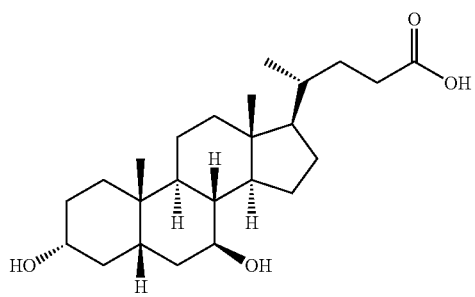

Ursodeoxycholic acid, also known as ursodiol, shows organotropism for the hepatoportal circuit. Because of this, ursodeoxycholic acid may be used to introduce molecules to the liver and the liver's pathways. Ursodeoxycholic acid is primarily used by the body to help digest fats and regulates cholesterol by reducing the rate at which the intestine absorbs cholesterol molecules while breaking up micelles containing cholesterol. This feature of ursodeoxycholic acid is also helpful in patients with gallstones that would like an alternative to surgery. Ursodeoxycholic acid is also currently the only FDA approved drug for the treatment of primary biliary cirrhosis. However, because of ursodeoxycholic acid's effects as in inhibiting apoptosis, it is not thought of to be used in the treatment of cancer which often features inducing apoptosis of cancer cells.

Various chemicals may be used in order to combine berberine and ursodeoxycholic acid. Some solvents comprise: DMF; diethyl ether; MeOH; CHCl3; DCC; and DMP. Additionally, several reagents may be used to directly modify and add onto berberine and its intermediaries in order to create NABR01. Furthermore, neutral alumina columns and thin layer chromatography plates may be used to purify and concentrate desired molecules are various stages of the synthesizing process. Additional methods may be used to purify and concentrate the desired products. Substitutions of the various solvents, reagents, and catalysts may be used. Often, these substitutions may be of a similar family or possess similar characteristics.

DMF is a polar aprotic solvent with a high boiling point and has the molecular structure:

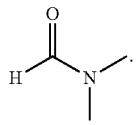

DMF is typically colorless and miscible with water and commonly used as a solvent for chemical reactions. DMF is short for dimethylformamide Diethyl ether is an organic compound in the ether class and has the following molecular structure:

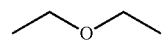

Diethyl ether is typically colorless and is a highly volatile flammable liquid. It is commonly used as a solvent and was once used as an anaesthetic. Since its original discovery and use, it has been discovered that diethyl ether has narcotic properties and its use may lead to addiction, known as etheromania.

MeOH is an organic compound in the alcohol class and has the following molecular structure:

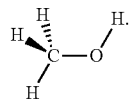

MeOH is typical colorless and is the simplest alcohol. MeOH is short for methanol. It is light, volatile, and flammable, similar to ethanol. MeOH is a polar liquid and often used as a solvent.

CHCl3 is a chloromethane commonly known as chloroform and has the following molecular structure:

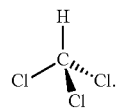

CHCl3 is an organic compound, sweet smelling and fairly dense. CHCl3 is also somewhat hazardous and is often portrayed as a chemical used in order to render a person unconscious. Additionally, CHCl3 may be fatal if too much is used which is one of the reasons CHCl3 fell out of favor as use as an anaesthetic.

DCC is an organic compound and has the following molecular structure:

DCC is often a white crystal with a sweet odor and is commonly used to couple amino acids in artificial peptide synthesis. DCC is short for N—N' -dicyclohexylcarbodiimide One possible mechanism for DCC used in the present invention is that DCC may activate the terminal OH in the carboxyl group of the ursodeoxycholic acid 145, allowing for the terminal amine of the berberrubine-9-hexyl amine 140 to attack the carbon on the hydroxyl group of the ursodeoxycholic acid 145.

DMP is a derivative of pyridine and has the following molecular structure:

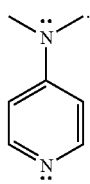

DMP is often a colorless solid and useful as a nucleophilic catalyst. DMP is short for 4-dimethylaminopyridine. DMP's catalytic function is often used as an acyl transfer catalyst in conjunction with DCC, commonly known as a Steglich esterification.

The Steglich esterification process allows for the formation of esters under relatively mild conditions. First DCC activates the carboxyl acid, and then DMP acts as an acyl transfer catalyst as follows:

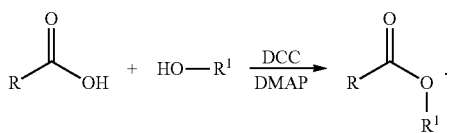

When the Steglich esterification process is used with an amine, the reaction occurs as follows:

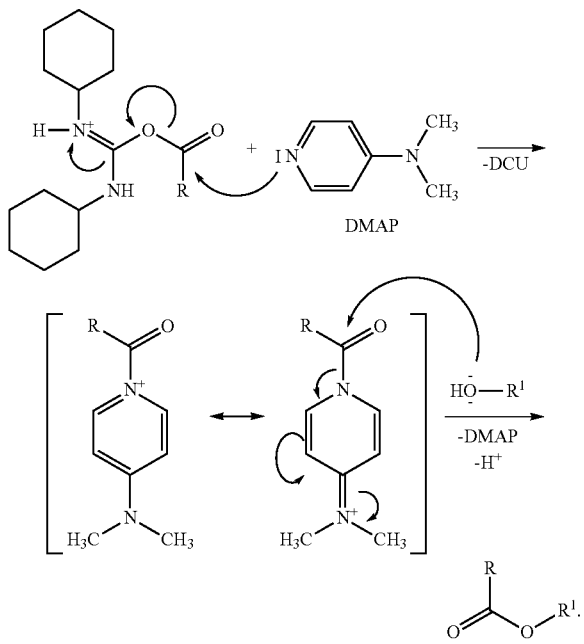

If the Steglich esterification process is used with an amine and proceeds at a relatively slow rate, a side-reaction with an undesirable side-product may occur. This side reaction is a 1,3-rearrangment of the O-acyl intermediate to an N-acyl urea which is unable to further react with an alcohol. The second reaction occurs when the Steglich esterification process proceeds at a relatively slow rate, allowing the desired product to undergo FIG. 1 is a flow diagram showing one method of synthesizing one embodiment of the invention. As shown in FIG. 1, one embodiment of the invention preferably comprises starting off with a berberine molecule 100 and performing various steps until NABR01 155 has been synthesized. Preferably, the berberine molecule undergoes a first reaction condition 105 which comprises heating the berberine molecule 100 to 190 C. for 90 minutes at 20-30 mmHG. It is understood that the first reaction condition 105 may utilize different temperatures, times, and pressures to obtain substantially the same result. Preferably, exposing the berberine molecule 100 to the first reaction condition 105 results in the formation of a berberrubine molecule 110, which is recovered by cooling and recrystallization from ethanol. In one embodiment of the invention, 10 g of berberine chloride 100 results in 8.37 g of berberrubine chloride 110.

Preferably, the berberrubine molecule 110 is then mixed with a first reactant 115 in DMF as a solvent under a second reaction condition 120 which comprises heating to 60 C. for 5 hours. Preferably, the first reactant 115 is 1,6-dibromohexane. Preferably, exposing the berberrubine molecule 110 to the first reactant 115 under a second reaction condition 120 results in the formation of a berberrubine-9-hexylbromide 125, which is preferably obtained by diluting with diethyl ether and filtering. Preferably, if a more pure formation of the berberrubine-9-hexybromide 125 is desired, a neutral alumina column with 5% MeOH and 95% CHCl3 as an eluent may be used.

In one embodiment of the invention, if 2 g of berberrubine chloride 110, 18 mL of DMF, 1.88 mL of 1,6-dibromohexane is used, followed by a diethyl ether dilution and diethyl ether wash results in 3 g of a crude product, which when purified by neutral alumina (Merck: 6176840) column chromatography (30 mm diameter, 110 mm length) with a 5% MeOH/95% CHCl3 eluent results in 2.15 g of berberrubine-9-hexyl bromide 125.

Preferably the berberrubine-9-hexylbromide 125 is mixed with a second reactant 130 under a third reaction condition 135 which comprises heating to 70 C. for 5 hours. Preferably, the second reactant 130 is ammonia and ammonium chloride. Preferably the ammonia is a 25% aqueous ammonia solution and the ammonium chloride is a solid. Preferably, MeOH is used as a solvent. Preferably, this results in the formation of a berberrubine-9-hexylamine 140 which may be obtained by evaporating and then purifying on a neutral alumina column using a gradient elution using 5% MeOH and 95% CHCl3 to 12% MeOH and 88% CHCl3.

In one embodiment of the invention, 1.5 g of berberrubine-9-hexyl bromide 125 is taken in 75 mL of MeOH, to which 57.5 mL of 25% aqueous ammonia and 1.43 g of ammonium chloride is added, which when purified by neutral alumina (Merck: 6176840) column chromatography (30 mm diameter, 110 mm length) utilizing a 5-12% MeOH and 95-88% CHCl3 gradient eluent, results in 0.59 g of berberrubine-9-hexyl amine 140.

Preferably, the berberrubine-9-hexylamine 140 is mixed with a third reactant 145 under a fourth reaction condition 150 which comprises stirring at room temperature for 24 hours. Preferably, the third reactant 145 is an ursodeoxycholic acid. Preferably DMF, DCC, and DMP are used as solvents and reaction catalysts. Preferably, this results in the formation of NABR01 155 which may be obtained by using a neutral alumina column, eluted with 10% MeOH and 90% CHCl3, concentrating the positive fractions and purified further by using thin layer chromatography. Preferably, the thin layer chromatography plates are 20×20×.05 cm and coated with silica gel 60 F254.

In one embodiment of the invention 0.2 g of berberrubine-9-hexyl amine 140, 171 mg of ursodeoxycholic acid, 126 mg of DCC and 74 mg of DMP are dissolved in DMF and stirred for 24 hours. Diethyl ether may then be added and the resulting solution may be filtered, resulting in a solid product. The solid product may then be initially purified by using neutral alumina (Merck: 6176840) column chromatography (18 mm diameter, 90 mm length) utilizing a 10% MeOH and 90% CHCl3 eluent to create a purified product, which may then be purified and concentrated by using preparative thin layer chromatography using plates coated with silica gel 60 F254, with dimensions 20×20×0.05 cm which may result in recovering 192 mg of NABR01 155.

Figure 2:
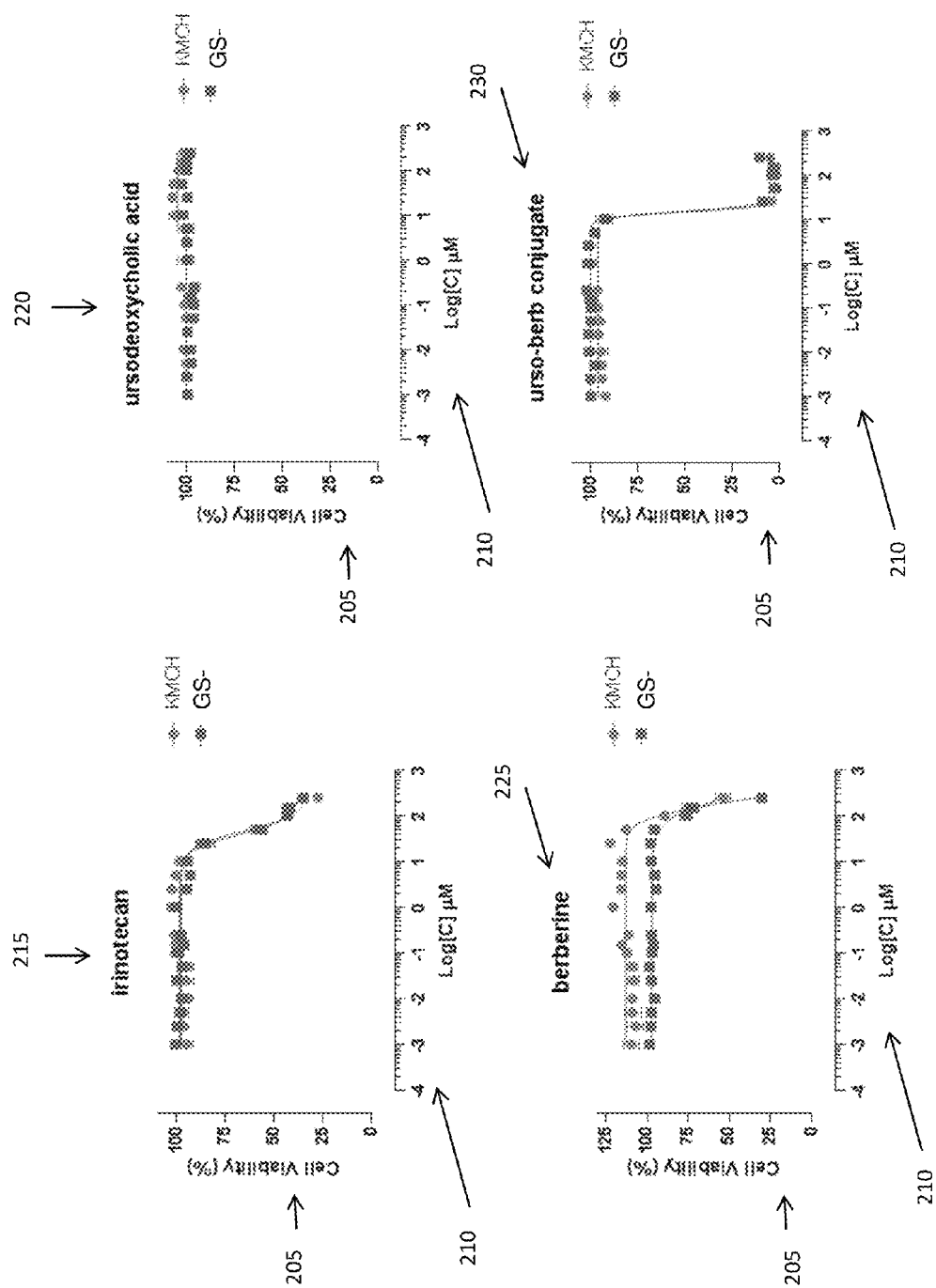
FIG. 2 is a set of graphs showing the IC50 of various molecules in KMCH and GS-Li013 cells.

FIG. 2 is a set of graphs showing the ability of various molecules to kill KMCH and GS-Li013 cells, which are cholangiocarcinoma cells. The data presented in FIG. 2 is based on in-vtro studies. The y-axis of each graph represents the Cell viability percentage 205 of KMCH and GS-Li013 cells. The x-axis of each graph represents the Log[C]210. [C] refers to the concentration of the molecule tested in uM. IC50 commonly refers to the half maximal inhibitory concentration, and is used to numerically represent the efficacy of various molecules to be effective in their respective tasks. In this case, IC50 means the concentration at which half of the target cells are no longer viable. Thus, the lower the IC50 value is, the more effective the molecule is in accomplishing what is being measured, in this case, killing cholangiocarcinoma cells. The unit uM is used to represent the IC50 value. uM is the same as micro molar concentration, which is $10^{-6}$ moles/liter, a common concentration unit.

As shown in FIG. 2, the IC50 of four molecules were determined over 24 hour period treatment. The first molecule, irinotecan, shown in the irinotecan graph 215, is a known chemotherapy drug used on cholangiocarcinoma cells, and has an IC50 of 90 uM when used on GS-cell lines and an IC50 of 95 uM when used on KMCH cell lines. The second molecule, ursodeoxycholic acid, shown in the ursodeoxycholic acid graph 220, may be a primary component in NABR01, is not cytotoxic on its own, and accordingly, as shown, has no IC50 on both KMCH and GS-cell lines. The third molecule, berberine, shown in the berberine graph 225, may be a primary component in NABR01, and has an IC50 of 200 uM on both KMCH and GS-cell lines. This shows that berberine has some cytotoxic ability, but is not as effective as irinotecan. The fourth molecule, urso-berb conjugate, also referred to as NABR01, shown in the urso-berb graph 230, has an IC50 of 15 uM on both KMCH and GS-cell lines. The IC50 of NABR01 is much lower than berberine, the main cytotoxic component, and the IC50 of NABR01 is even lower than irinotecan. Thus, the combination of two relatively ineffective molecules is able to be more effective than the known and used molecule irinotecan. Thus, this data shows that the IC50 of NABR01 is much lower than one would expect, and shows an unexpectedly high effectiveness of NABR01. Additionally, because the IC50 of NABR01 is much lower than the known drug irinotecan, NABR01 is effective at killing cholangiocarcinoma cells.

To obtain the data in FIG. 2, Cell Counting Kit-8 (CCK-8) was used. CCK-8 is commercially available from Dojindo Molecular Technologies, Inc. CCK-8 allows sensitive colorimetric assays for the determination of cell viability in cell proliferation and cytotoxicity assays. Dojindo's highly water-soluble tetrazolium salt, used in CCK-8, is reduced by dehydrogenase activities in cells to give a yellow-color formazan dye, which is soluble in the tissue culture media. The amount of the formazan dye, generated by the activities of dehydrogenases in cells, is directly proportional to the number of living cells. The detection sensitivity of CCK-8 may be higher than the other tetrazolium salts such as MTT, XTT, MTS or WST-1. Cancerous cells in a cell culture were exposed to the either irinotecan, ursodeoxycholic acid, berberine, or NABR01, and the results were recorded. Various concentrations of each molecule were used, resulting in different amount of cell viability. Cell viability was measured according to the procedures of CCK-8, namely higher cell counts lead to higher absorption measurements, which would mean lower drug efficacy.

Figure 3:
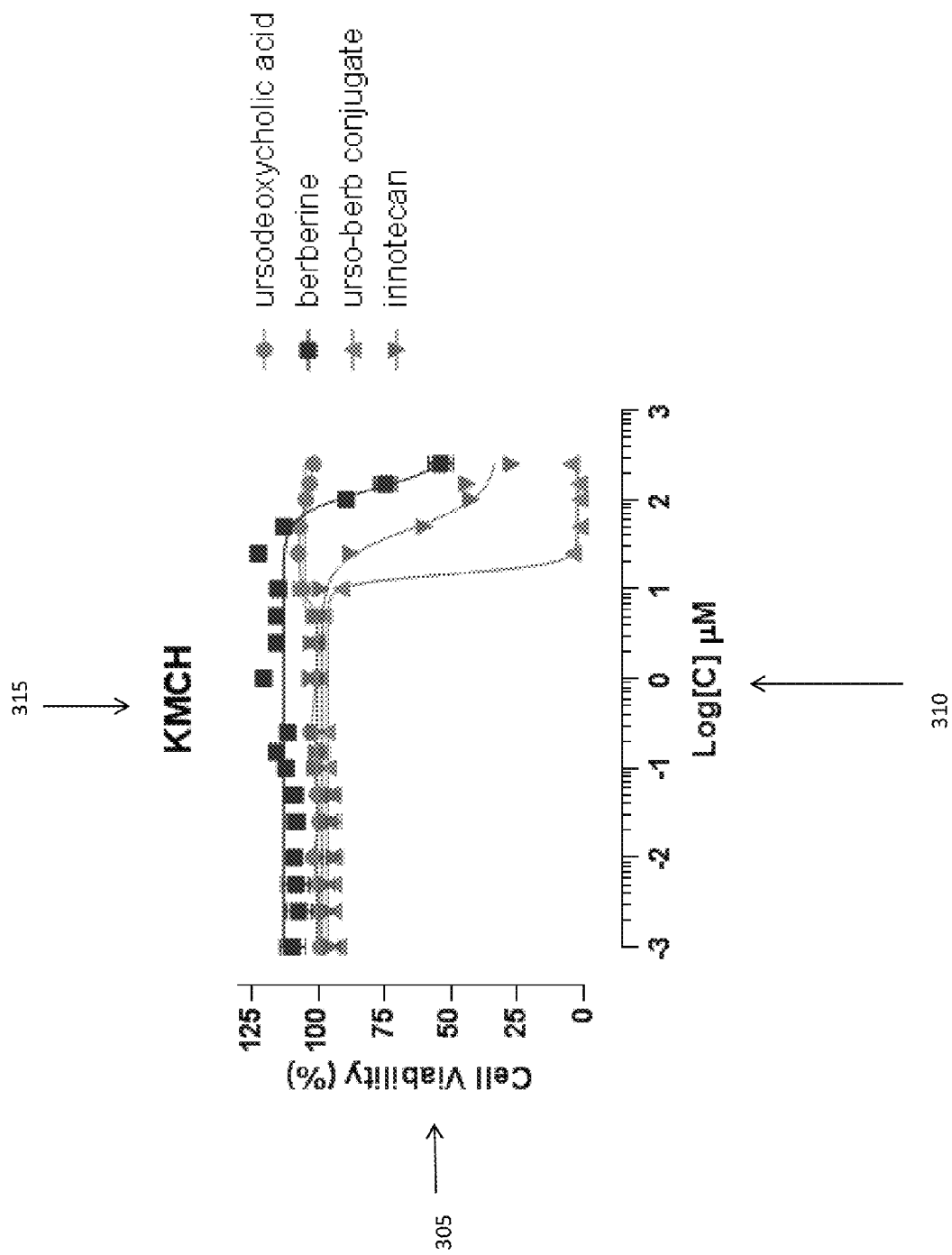
FIG. 3 is a graph which overlays data showing the IC50 of various molecules in KMCH cells.

FIG. 3 is a graph which overlays data showing the IC50 of various molecules in KMCH cells. As shown in FIG. 3, a KMCH graph 315 has a y-axis showing cell viability percentage 305 of KMCH cells and an x-axis showing the Log[C]310. [C] refers to the concentration of the various molecules tested in uM. The data presented in FIG. 3 is based on in-vtro studies. As visually depicted in FIG. 3, the IC50 of NABR01 is significantly lower than either of NABR01's components, berberine and ursodeoxycholic acid, when used on KMCH cell lines. Additionally, the IC50 of NABR01 is significantly lower than irinotecan, a known chemotherapy drug.

Figure 4:
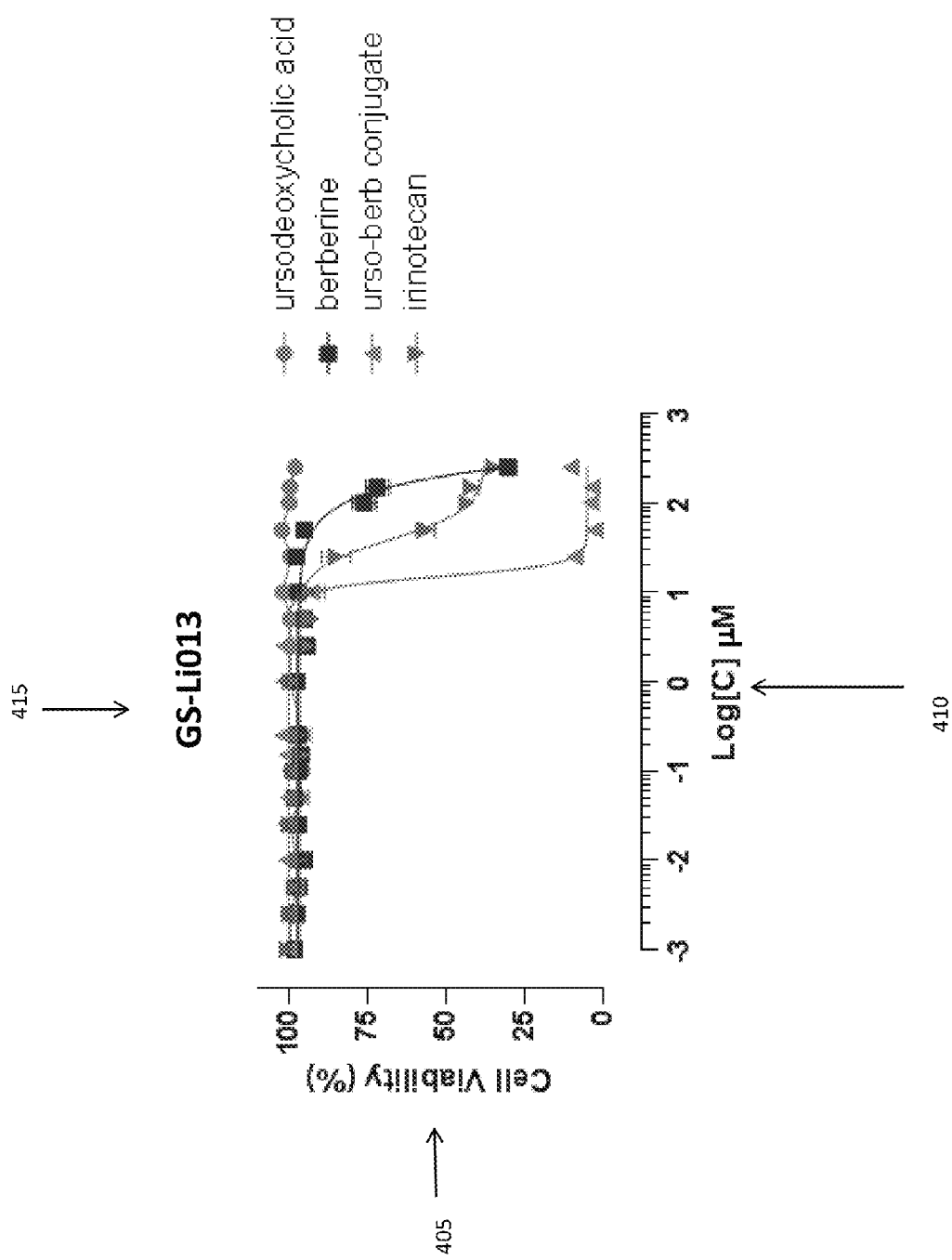
FIG. 4 is a graph which overlays data showing the IC50 of various molecules in GS-Li013 cells.

FIG. 4 is a graph which overlays data showing the IC50 of various molecules in GS-LI013 cells. As shown in FIG. 4, a GS-LI013 graph 415 has a y-axis showing cell viability percentage 405 of GS-LI013 cells and an x-axis showing Log[C] 410. [C] refers to the concentration of the various molecules tested in uM. The data presented in FIG. 4 is based on in-vtro studies. As visually depicted in FIG. 4, the IC50 of NABR01 in GS-LI013 cells is significantly lower than either of NABR01's components, berberine and ursodeoxycholic acid, when used on GS-LI013 cell lines. Additionally, the IC50 of NABR01 is significantly lower than irinotecan, a known chemotherapy drug, in GS-LI013 cells.

In one embodiment of the invention, certain positions on NABR01 may have additional or different R functional groups at various points on the molecule. An R functional group is commonly used as shorthand for an atom or chain of atoms which are attached to a molecule. One embodiment of the invention showing the placement of an R functional group is shown below.

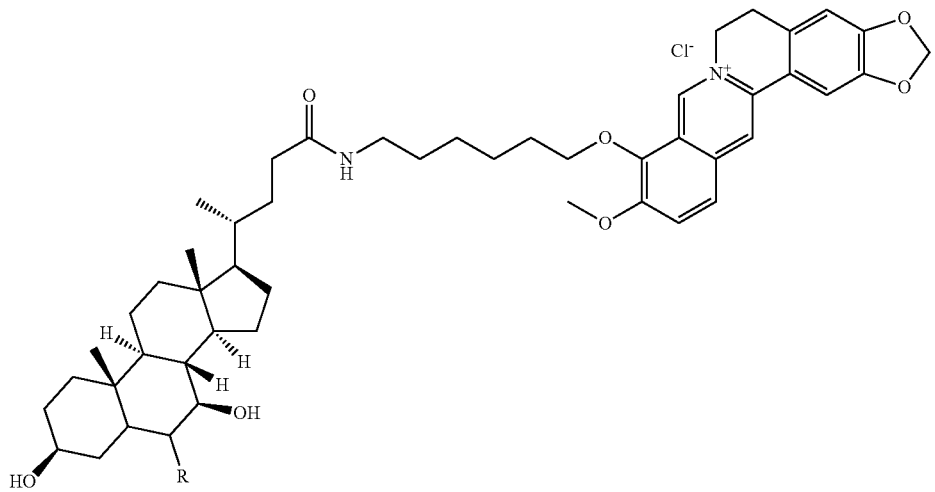

The molecule above may be synthesized by simply substituting the ursodeoxycholic acid from the synthesis of NABR01 with an ursodeoxycholic acid that already has the desired R functional group.

In another embodiment of the invention, the R functional group may be an ethyl group. This embodiment may be known as berberrubine-6-ethyl ursodeoxycholic acid and may have the molecular structure as shown below. The ethyl group is a two carbon chain saturated with hydrogen connected to a carbon of the NABR01.

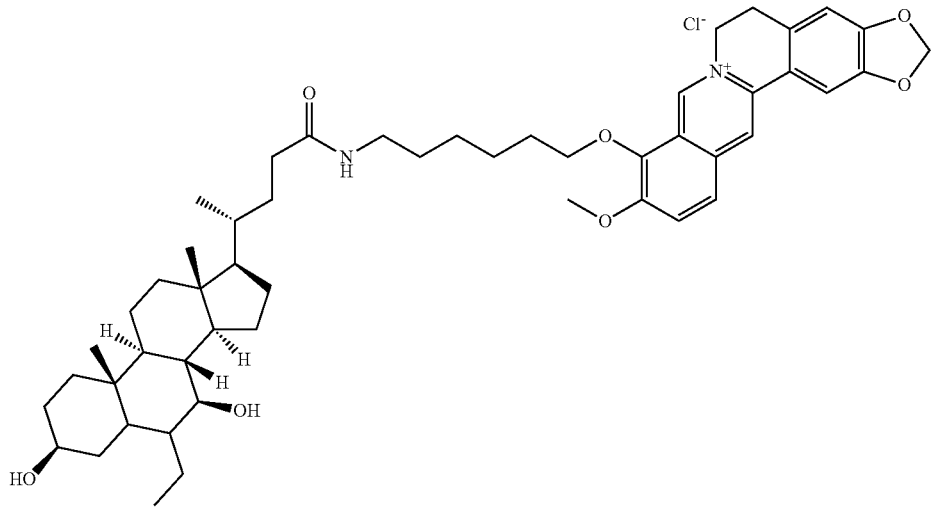

In other embodiments of the invention, additional R functional groups may be added to NABR01. Not only may the R functional groups be added to disclosed attachment sites as in the molecule above, but the R functional groups may be added to any portion of the NABR01. Components of the NABR01 may be purchased commercially with the desired R functional groups already attached.

Figure 5:
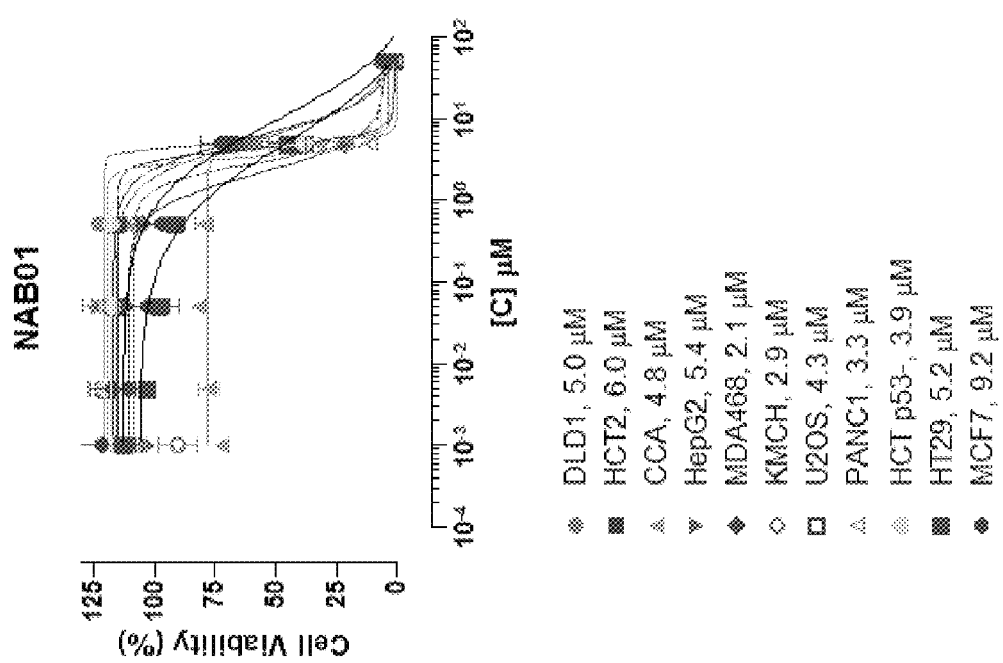
FIG. 5 is a graph which overlays data showing the IC50 of NABR01 with various cancerous cell lines over a 48 hour period.
Figure 6:
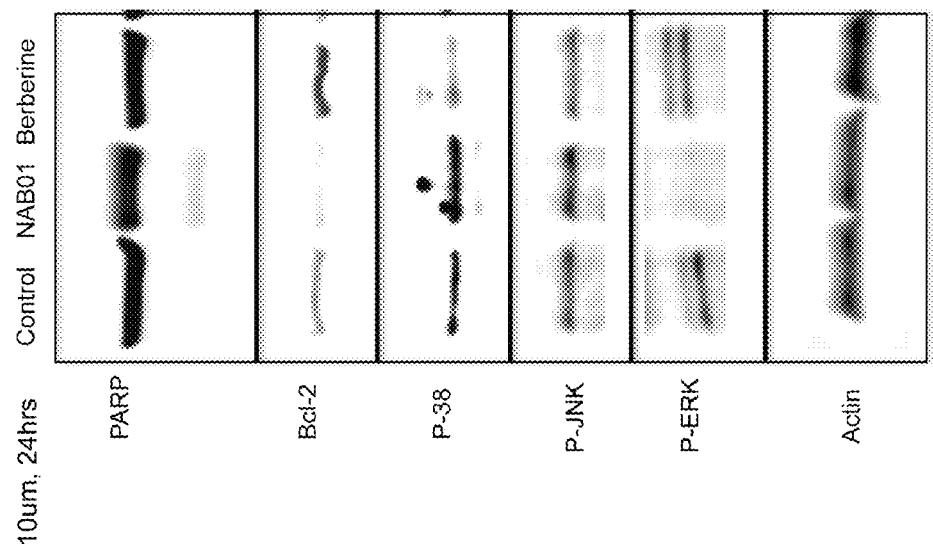
FIG. 6 is an illustration of a Western Blot analysis showing the effect of NABR01 at 10 uM over 24 hours on PARP, Bcl-2, P-38, P-JNK, P-ERK, and Actin.
Figure 7:
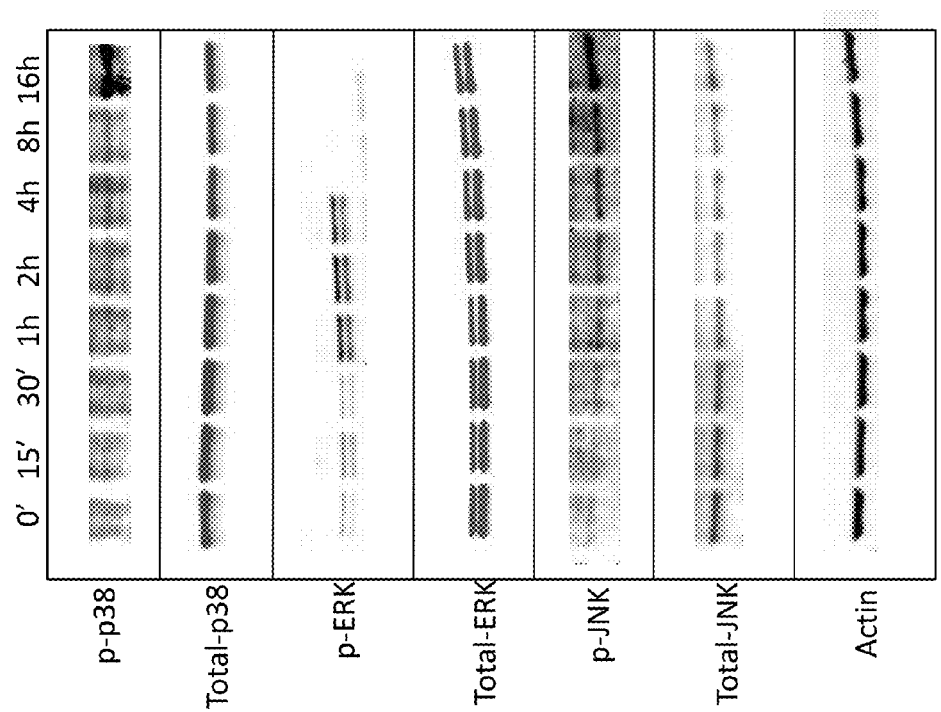
FIG. 7 is an illustration of a Western Blot analysis showing the effect of NABR01 at 10 uM over 16 hours on P-38, P-JNK, P-ERK, and Actin.
Figure 8:
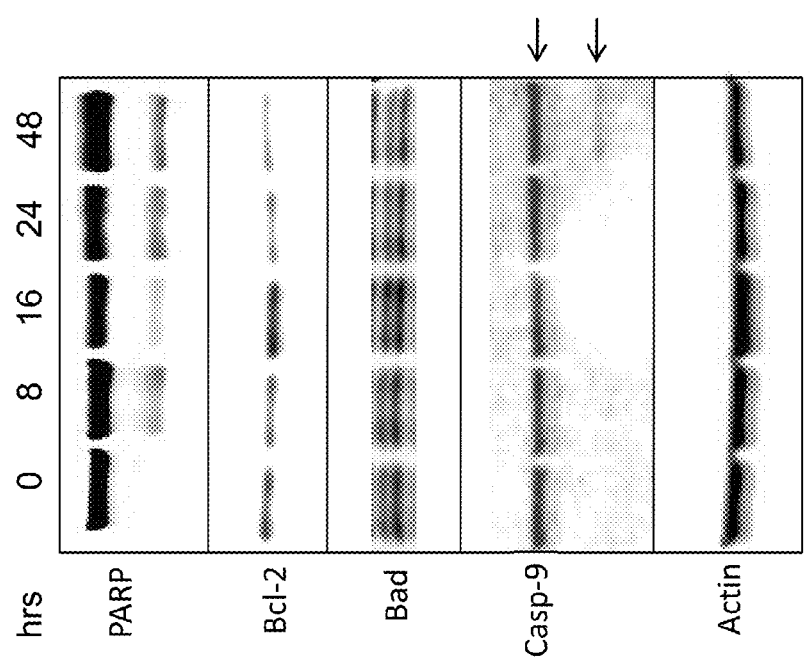
FIG. 8 is an illustration of a Western Blot analysis showing the effect of NABR01 at 10 uM over 48 hours on PARP, Bcl-2, Bad, Casp-9, and Actin, which attention drawn to Casp-9.
Figure 9:
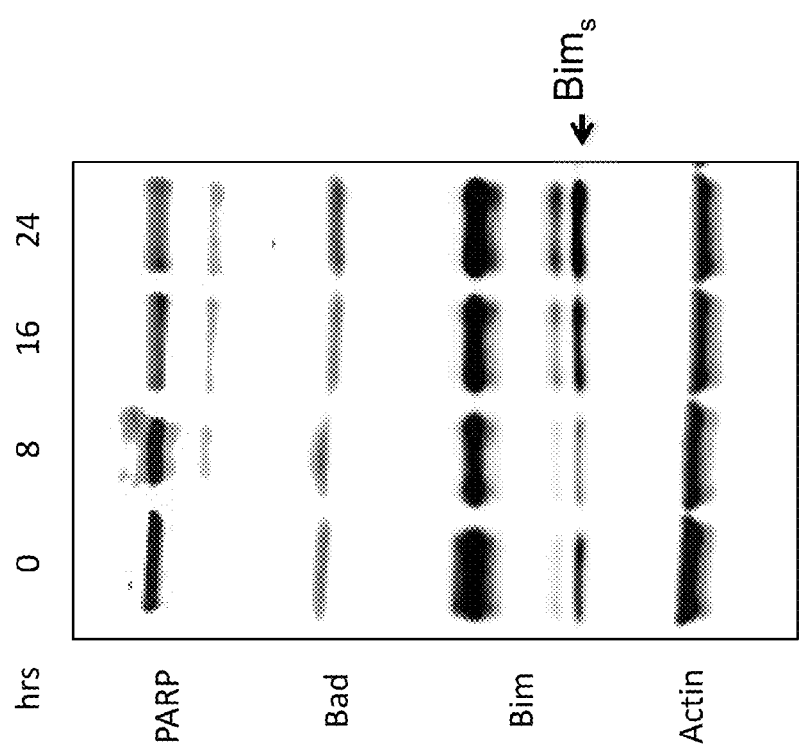
FIG. 9 is an illustration of a Western Blot analysis showing the effect of NABR01 at 10 uM over 24 hours on PARP, Bad, Bim, and Actin, with attention drawn to Bim-s.
Figure 10:
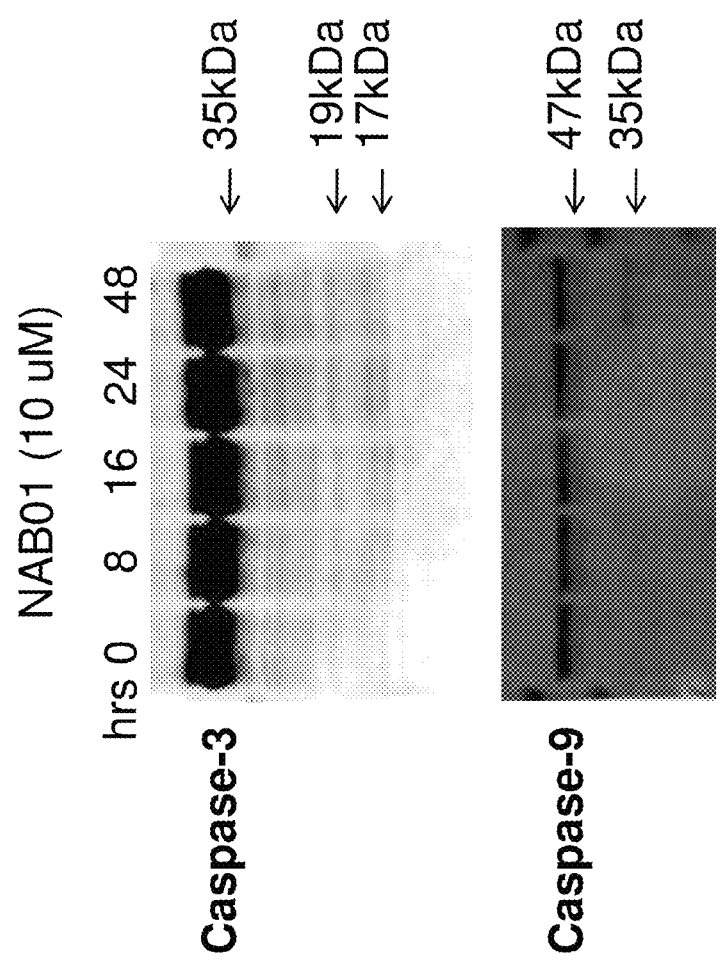
FIG. 10 is an illustration of a Western Blot analysis showing the effect of NABR01 at 10 uM over 48 hours on Caspase-3 and Caspase-9.
Figure 11:
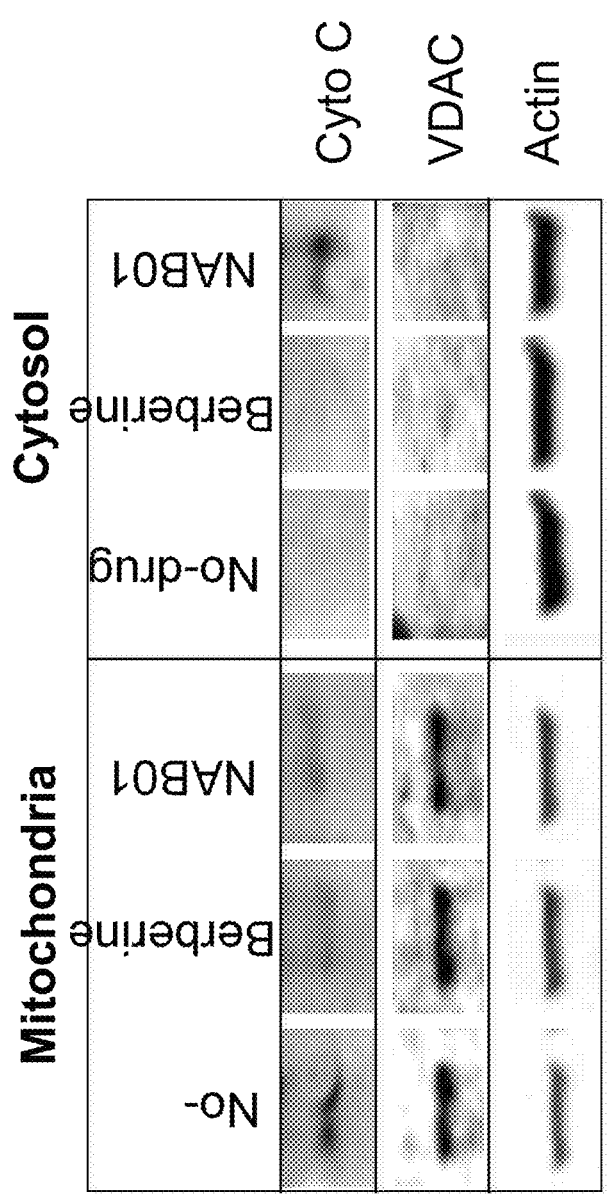
FIG. 11 is an illustration of a Western Blot analysis showing the effect of No-drug, berberine, and NABR01 on the levels of Cyto C, VDAC, and Actin in the mitochondria and cytosol.
Figure 12:
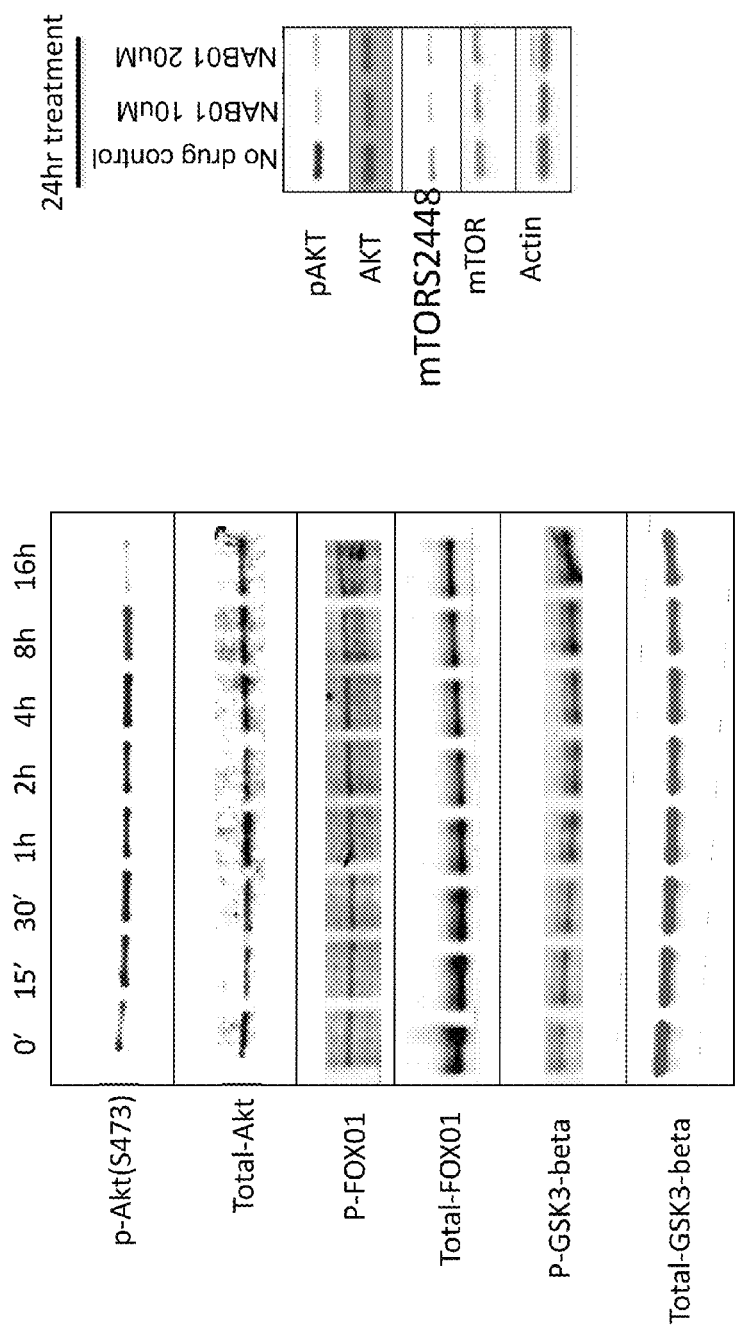
FIG. 12 is an illustration of a Western Blot analysis showing the effect of No-drug, NABR01, and berberine at 10 uM over 16 hours on Akt, FOX01, and GSK3-beta.
Figure 13:
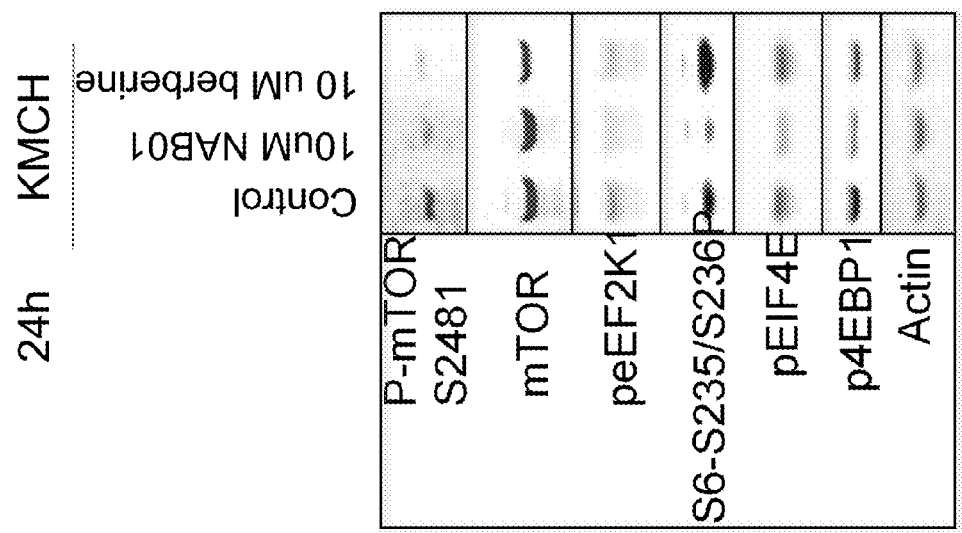
FIG. 13 is an illustration of a Western Blot analysis showing the effect of NABR01 over 24 hours on mTOR, peEF2k1, S6-S235/S236P, EIF4E, EBP1, and Actin.
Figure 14:
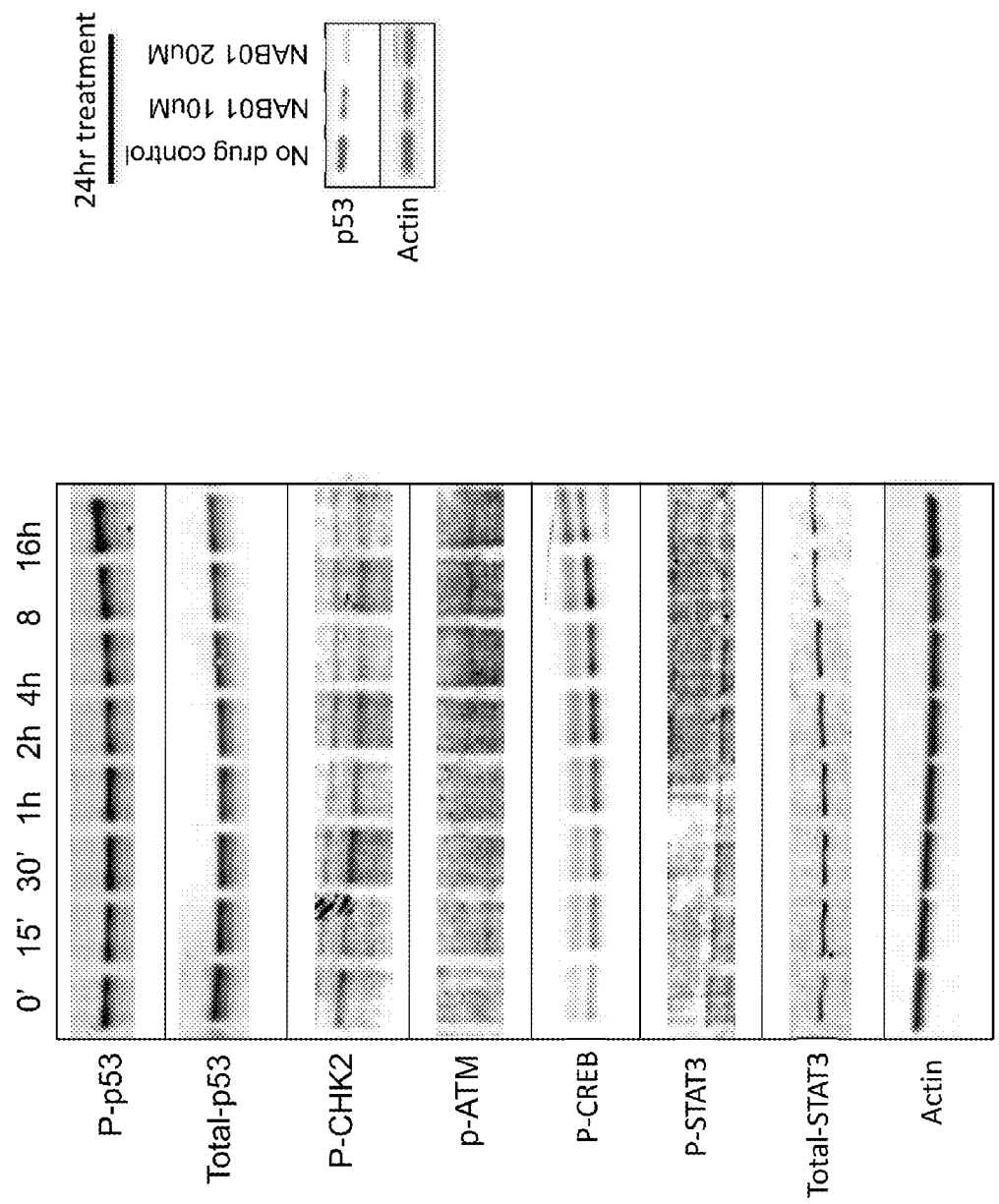
FIG. 14 is an illustration of a Western Blot analysis showing the effect of NABR01 over 16 hours on p53, CHK2, ATM, CREB, STAT3, and Actin.
Figure 15:
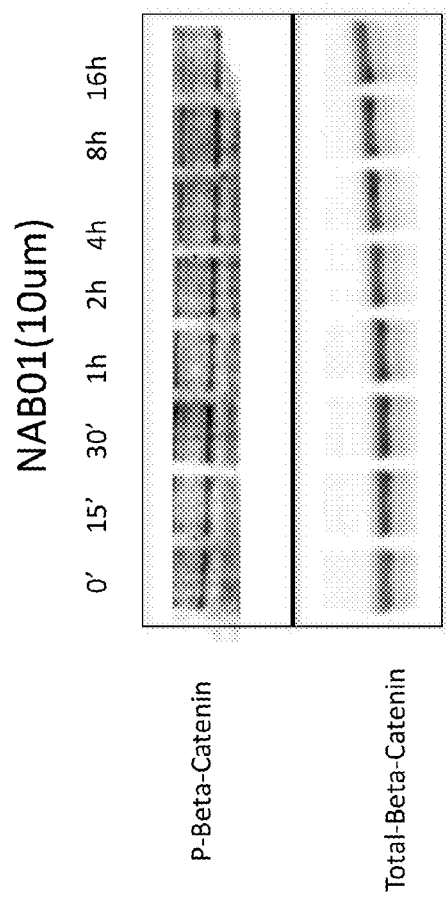
FIG. 15 is an illustration of a Western Blot analysis showing the effect of NABR01 at 10 uM over 16 hours on Beta-Catenin
Figure 16:
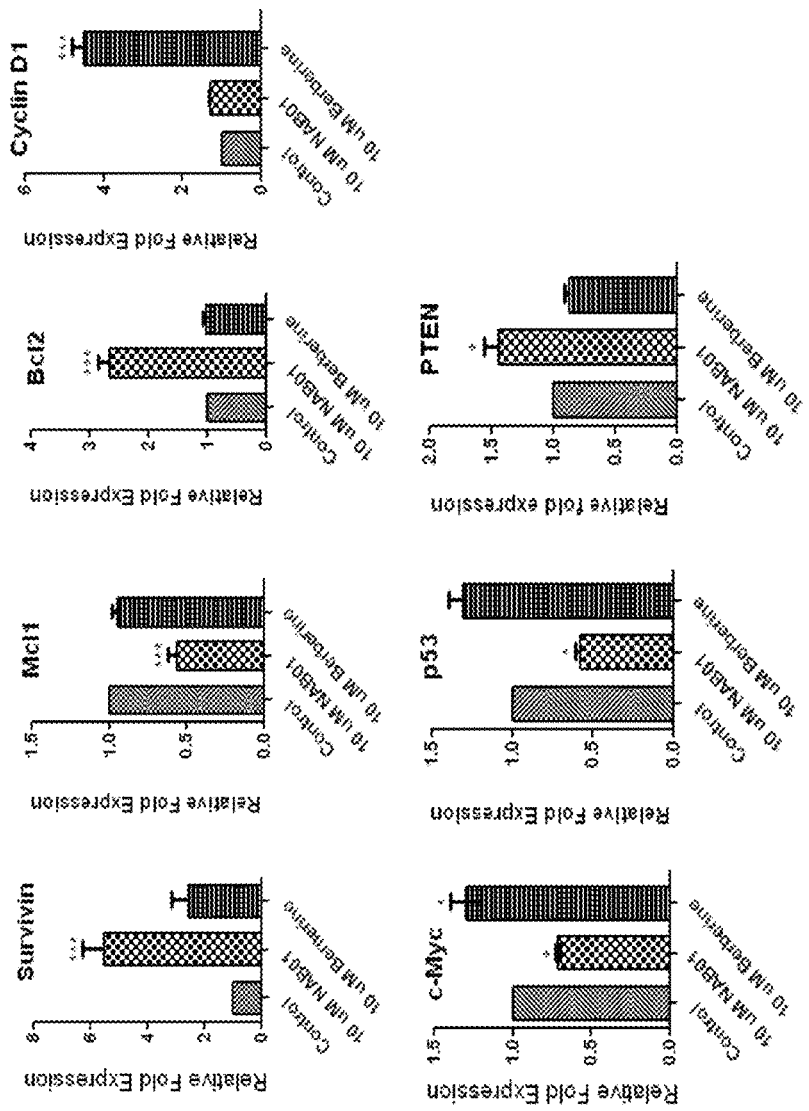
FIG. 16 is a series of graphs showing gene expression in Control, NABR01, and Berberine treated KMCH cells for Survivin, Mc11, Bc12, Cyclin D1, c-Myc, p53, and PTEN.
Figure 17:
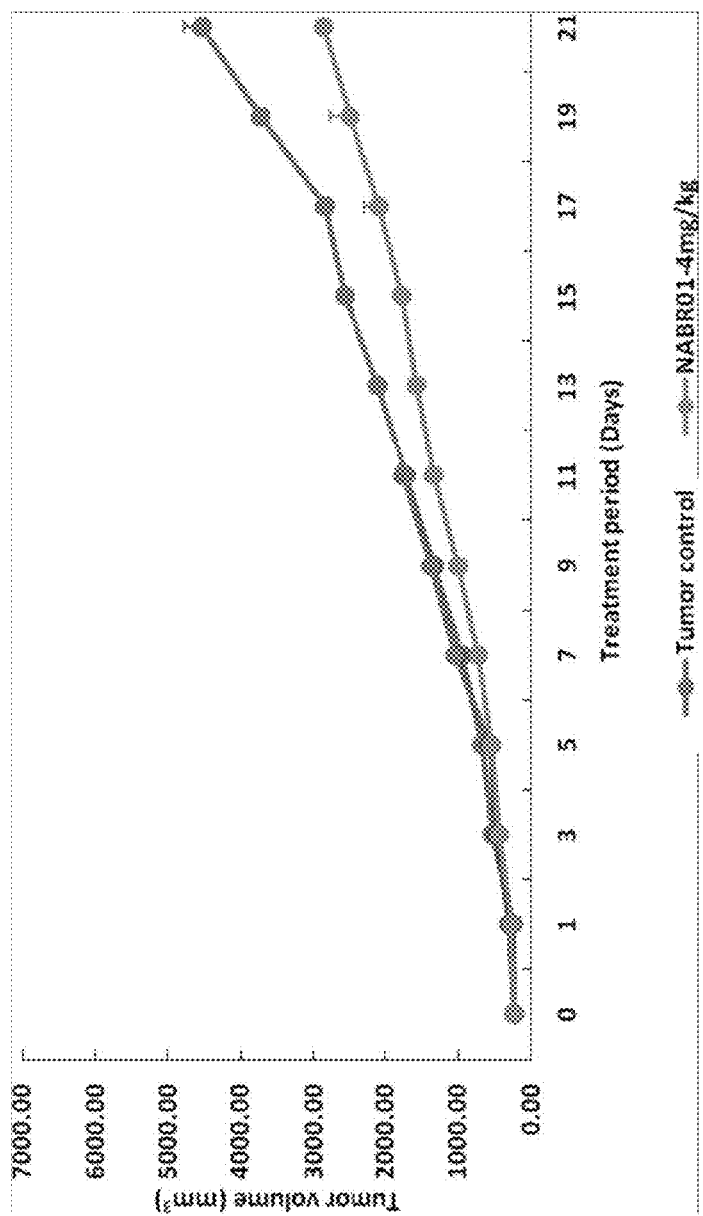
FIG. 17 is a graph showing the growth of a tumor under control and NABR01 treated conditions.

FIG. 5 is a graph which overlays data showing the IC50 of NABR01 with various cancerous cell lines over a 48 hour period. As shown in FIG. 5, NABR01 has an unusually high efficacy on several cell lines, with an IC50 of less than 10 uM as measured through CCK-8 methodology, described above. DLD1 refers to Dukes' type C, colorectal adenocarcinoma, and NABR01 has an IC50 of 5.0 uM for DLD1. HCT2 refers to a hamster lymphoid cell line, and NABR01 has an IC50 of 6.0 uM for HCT2. CCA refers to a cholangiocarcinoma cell line, and NABR01 has an IC50 of 4.8 uM for CCA. HepG2 refers to a hepatocellular carcinoma cell line, and NABR01 has an IC50 of 5.4 uM for HepG2. MDA468, also known as MDA-MB468, refers to a triple negative adenocarcinoma cell line of the breast, and NABR01 has an IC50 of 2.1 uM for MDA468. KMCH refers to a hepatocellular and cholangiocarcinoma cell line, and NABR01 has an IC50 of 2.9 uM for KMCH. U2OS refers to a sarcoma of the tibia cell line, and NABR01 has an IC50 of 4.3 uM for U2OS. PANC1 refers to an epithelioid carcinoma cell line, and NABR01 has an IC50 of 3.3 uM for PANC1. HCT refers to a colorectal carcinoma cell line, and NABR01 has an IC50 of 3.9 uM for HCT. HT29 refers to a colorectal adenocarcinoma cell line, and NABR01 has an IC50 of 5.2 uM for HT29. MCF7 is an adenocarcinoma cell line of the breast, and NABR01 has an IC50 of 9.2 uM. NABR01 has an unexpectedly effective IC50 of less than 10 uM for the cell lines described above, and the related cancers.

FIGS. 6-18 is data which illustrates the mechanism of action for NABR01. Once a mechanism of action is known, it may become possible to predict with some level of accuracy the effects a drug may have, though extensive testing would still be required. Until a mechanism is known, it is extremely difficult to predict what a particular molecule or compound may be useful for, if it is even useful at all. A western blot analysis was performed for MAP kinase signaling proteins, phospho p38, phospho JNK and phospho ERK in KMCH cells with and without NABR01 treatment. The western blot analyses indicate that the cell survival pathway consisting of phospho ERK is downregulated while the cell death signaling pathways phospho p38 and phospho JNK increased. This result was not observed in cells when treated with Berberine alone.

Further, investigation found that PARP, a protein activated during cell death was activated by PARP's cleavage in NABR01 treated cells, unlike in berberine treated cells. Anti-apoptotic protein Bcl2 is also down regulated in cells treated with NABR01. The cytotoxic effect of NABR01 in addition to downregulation of Bcl2, may be attributed to an increase in proapoptotic protein Bim which is specifically cleaved to generate the cytotoxic Bims-form in KMCH cells are treated with NABR01. Caspase-9 is cleaved in cells treated with NABR01 indicating an upstream activation of Caspase 3. In response to NABR01 treatment in KMCH cells, cytochrome C may be released from mitochondria, whereas berberine at the same concentration levels of NABR01 tested did not result in the release of cytochrome C. Accordingly, not only does the ursodiol component of NABR01 assist in targeting, but ursodiol also increases efficacy of the compound when introduced directly to the relevant cells, a wholly unexpected effect.

Many other pathways that affect the survival and proliferation of cancer cells like phospho PTEN remain unchanged by NABR01 treatment. Certain other pathways that affect cancer cell proliferation were downregulated, such as the AKT signaling pathway, phosphor-AKT pathway, and phosphor mTOR 52481 pathway. Total P53 levels are downregulated with NABR01 treatment. Phospho CKH2 and phosphoATM, which are involved in DNA repair, may have increased activity in NABR01 treated cells, indicating that NABR01 may induce DNA damage. The activity of pro-inflammatory signaling pathway protein phospho STAT may also increase in NABR01 treated cells.

Molecules related to protein synthesis such as phospho p70S6 kinase, phospho eIF4E, phospho EF2k, and phospho 4EBP1 are not significantly altered by NABR01.

Figure 18:
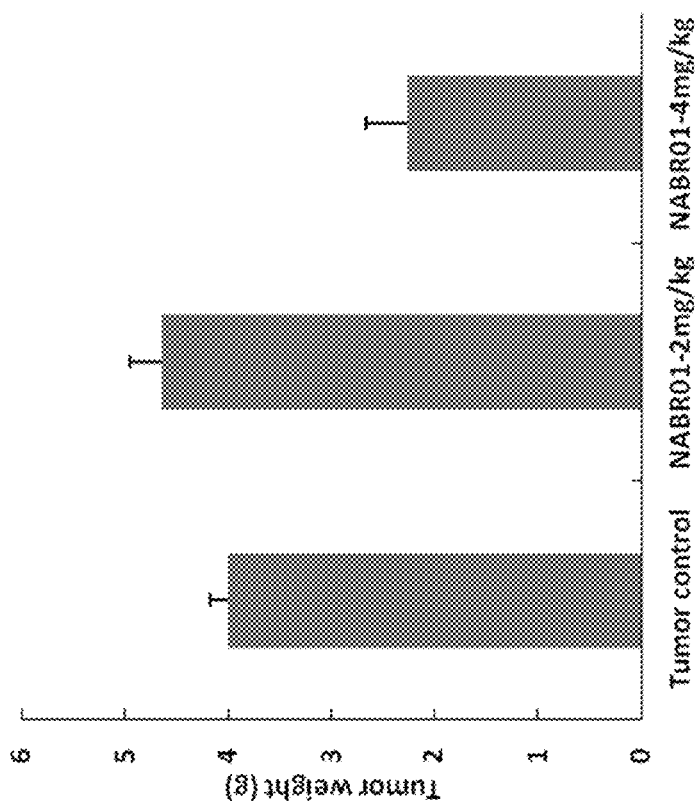
FIG. 18 is a graph showing the growth of a tumor under control, NABR01 at 2mg/kg, and NABR01 at 4mg/kg conditions.

Tumor xenografts studies in mice indicate that the tumor growth corresponding to weight and volume in NABR01 treated group of mice was reduced by approximately 45% in size when treated for 21 days. As shown in FIG. 18, mice with a KMCH tumor were treated with NABR01 in an amount of 4 mg/kg and showed a 43.46% tumor weight inhibition.

According to the figures and explanation presented above, it can be summarized that NABR01 activation of p38 protein by phosphorylation which leads to an increase in s-form (short form) pro-apoptotic protein Bims and Noxa. Additionally, NABR01 causes an decrease in Bcl2 levels. Gene expression studies indicate that activation of Bcl2 may be an attempt to compensate for the loss of protein. However, by 24hrs of exposure of NABR01, a significant decrease in Bcl2 protein levels may be observed. Activation of Caspases (caspase 9 and 3 western blot) leads to PARP activation (summary figure). Overall, NABR01 may cause cytotoxic effects on cholangiocarcinoma cell line KMCH in vitro and also in tumor xenografts studies. Accordingly, NABR01 can be a potential anti-cancer drug which may be used as a monotherapy or a combination therapy together with other chemo or target therapeutic drugs in treating cholangiocarcinoma.

Figure 19:
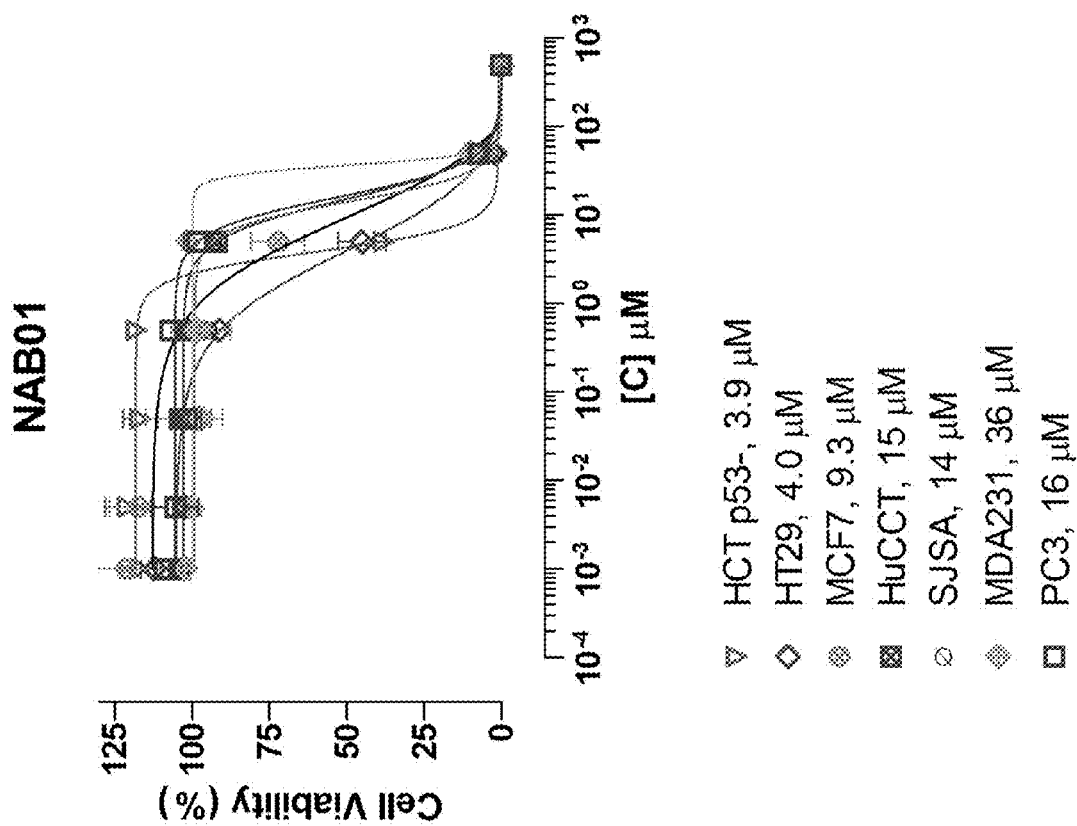
FIG. 19 is a graph which overlays data showing the 1050 of NABR01 in various cell lines.
Figure 20:
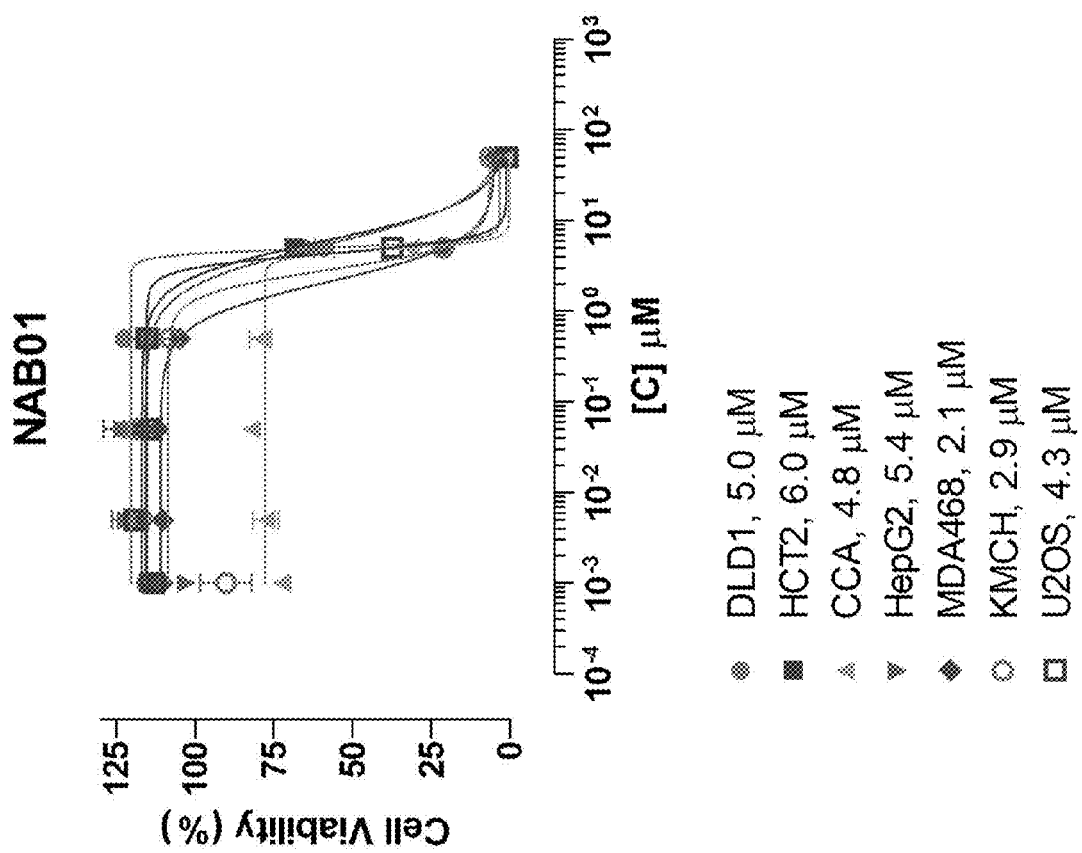
FIG. 20 is a graph which overlays data showing the 1050 of NABR01 in various cell lines

As shown in FIGS. 19-20, the efficacy of NABR01 can vary greatly depending on the cancerous cell line, and as a result, NABR01 may not be effective against certain cell lines. The data reflected in FIGS. 19-20 was collected over a 48 hour period, under the same conditions as the data shown in FIG. 5. When NABR01 has an IC50 of greater than approximately 10 uM, it can generally said to be less effective, and the higher than IC50 value, the less effective NABR01 is for that particular cell line. NABR01 can be considered effective for cell lines when its IC50, as measured under the present conditions and methods, is approximately 10 uM or lower. For example, NABR01 is not particularly effective on SJSA, HuCCT, PC3, and MDA231 cell lines. NABR01 has an IC50 of 14 uM for SJSA, 15 uM for HuCCT, 16 uM for PC3, and 36 uM for MDA231. Accordingly, the determination of for which cancer types are treatable by NABR01 is limited, and in order to determine which cancer types are treatable requires extensive research.

Figure 21:
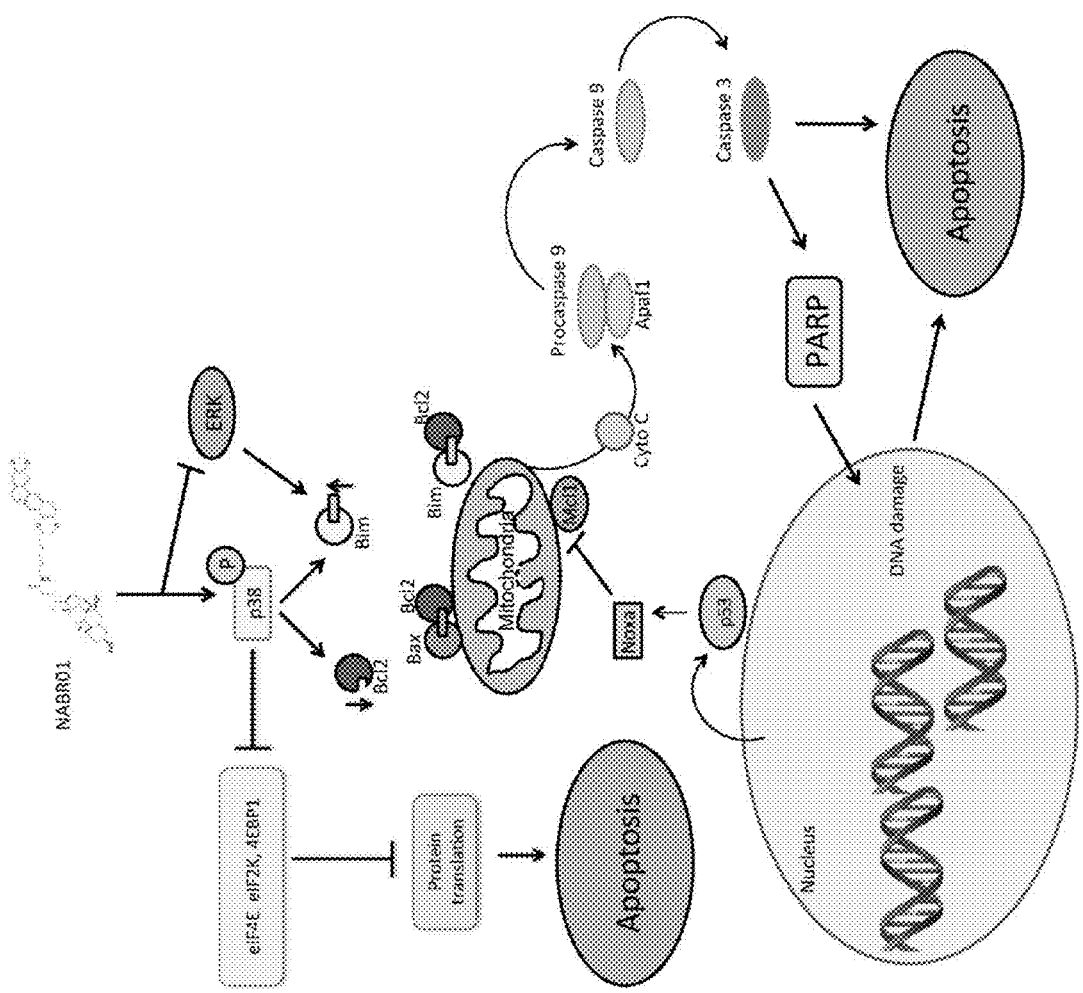
FIG. 21 shows one likely mechanism of activation for NABR01 that results in apoptosis.

FIG. 21 shows one likely mechanism of activation for NABR01 that results in apoptosis.

As described above, ursodeoxycholic acid is useful in the therapy of liver cancer and other liver ailments, including liver cirrhosis, primary sclerosing, cholangitis, cholelithiasis, non-alcoholic fatty liver disease, and non-alcoholic steatohepatitis. Also, because ursodeoxycholic acid is naturally produced by intestinal bacteria as a byproduct of primary bile acids, it demonstrates organotropism in the hepatoportal circuit. Berberine is a DNA binding molecule with general anti-cancer properties. By attaching berberine to ursodeoxycholic acid, the resulting conjugate has an increased uptake in the hepatoportal circuit while binding to and fighting cancer cells. Because many cancer fighting treatments induce apoptosis in cancer cells, cancer fighting treatment compounds are not typically combined with a molecule like ursodeoxycholic acid, which is itself believed to prevent apoptosis. Thus, the combination of these two molecules in use together would not be expected or intuitive. NABR01 may be taken orally, and then enter the hepatoportal circuit through the same mechanisms as ursodeoxycholic acid would.

NABR01 may also be combined with traditional chemotherapy for liver cancer. NABR01 may target the hepatic portal circuit, in addition to the liver specifically. This hepatic portal circuit includes, but is not limited to, organs such as the liver, gall bladder, duodenum, and small intestine.

Details such as quantity of items used, volume of solutions, temperatures, reaction times, filtration details, and all other aspects of the reaction may be variable. Much larger scales of production may also be used with substantially similar but adapted methods. The quantities and figures described herein refer to one of a multitude of methods to prepare the invention and analogs of the invention.

We claim:
1. A method of treating cancer comprising the steps:
identifying an individual having a cancer treatable by NABR01;
administering said individual with an effective amount of NABR01:

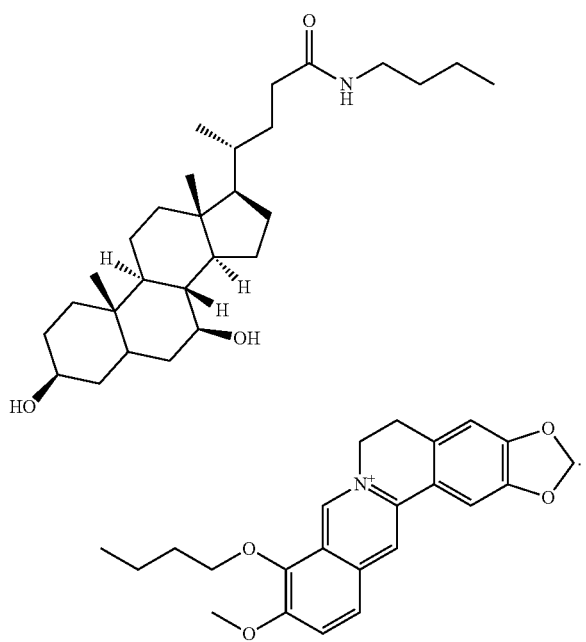

2. The method of claim 1, wherein said cancer treatable by NABR01 is a breast cancer.

3. The method of claim 1, wherein said cancer treatable by NABR01 is a liver cancer.

4. The method of claim 1, wherein said cancer treatable by NABR01 is a colorectal cancer.

5. The method of claim 1, wherein said cancer treatable by NABR01, when measured by CCK-8, has an IC50 of less than 10 uM when exposed to NABR01 for more than 48 hours.

6. The method of claim 1, wherein said cancer treatable by NABR01 is selected from the group consisting of the DLD1, HCT2, CCA, HepG2, MDA468, KMCH, U2OS, PANC1, HCT, HT29, and MCF7 cell lines.

7. The method of claim 6, wherein said administering of said individual with said effective amount of NABR01 is an oral administration.

8. The method of claim 6, wherein said administering of said individual with said effective amount of NABR01 is an intravenous administration.

9. The method of claim 1, wherein said effective amount of NABR01 is between approximately 2 mg per kg of said individual and approximately 6 mg per kg of said individual.

10. The method of claim 9, wherein said effective amount of NABR01 is approximately 4 mg per kg of said individual.

* * * * *